United States Patent
Cilingiroglu et al.

(10) Patent No.: US 10,282,510 B2
(45) Date of Patent: May 7, 2019

(54) ALIGNMENT OF CAD DATA TO IMAGES IN HIGH RESOLUTION OPTICAL FAULT ANALYSIS

(71) Applicant: FEI Company, Hillsboro, OR (US)

(72) Inventors: Tenzile Berkin Cilingiroglu, Fremont, CA (US); Neel Leslie, San Jose, CA (US)

(73) Assignee: FEI Company, Hillsboro, OR (US)

( * ) Notice: Subject to any disclaimer, the term of this patent is extended or adjusted under 35 U.S.C. 154(b) by 13 days.

(21) Appl. No.: 15/482,687

(22) Filed: Apr. 7, 2017

(65) Prior Publication Data

US 2018/0293346 A1    Oct. 11, 2018

(51) Int. Cl.
| | |
|---|---|
| *G06F 17/50* | (2006.01) |
| *G01N 21/95* | (2006.01) |
| *G06T 7/00* | (2017.01) |
| *G06T 7/60* | (2017.01) |
| *G01N 21/956* | (2006.01) |

(52) U.S. Cl.
CPC ..... *G06F 17/5081* (2013.01); *G01N 21/9501* (2013.01); *G06T 7/0004* (2013.01); *G06T 7/60* (2013.01); *G01N 2021/95615* (2013.01); *G06T 2207/30148* (2013.01)

(58) Field of Classification Search
USPC ........................................................ 716/111
See application file for complete search history.

(56) References Cited

U.S. PATENT DOCUMENTS

| | | | |
|---|---|---|---|
| 9,064,083 B2 | 6/2015 | Durec et al. | |
| 2007/0032896 A1* | 2/2007 | Ye | G03F 7/705 700/108 |
| 2010/0251202 A1* | 9/2010 | Pierrat | G03F 1/36 716/50 |
| 2014/0047396 A1 | 2/2014 | Durec et al. | |
| 2014/0172345 A1* | 6/2014 | Stoker | G01N 21/95 702/117 |

OTHER PUBLICATIONS

Cilingiroglu, T.B. et al., "Dictionary based Image Reconstruction for Superresolution in Integrated Circuit Imaging," Optics Express, Jun. 2015, vol. 23, Issue 11, pp. 15072-15087.

(Continued)

*Primary Examiner* — Mohammed Alam
(74) *Attorney, Agent, or Firm* — Denton W. McAlister

(57) ABSTRACT

In one embodiment, a method for improving the alignment of CAD data to optical imaging data, such as LSM and LVI images of integrated circuits is disclosed. Image reconstruction techniques are applied to optical images, such as laser voltage images (LVI), laser scanning microscope (LSM) images, or emission images, to produce reconstructed images which may have higher resolution, increased signal-to-noise, or other enhancements. Multiple CAD pattern layers are processed to generate second CAD images more closely corresponding to the appearance of the reconstructed images. Alignment of the reconstructed images to the second CAD data may be substantially more accurate and precise than alignment of the initial optical images to the CAD data—in some cases this improvement may make the difference between a successful alignment and a failed alignment.

21 Claims, 18 Drawing Sheets

(56) References Cited

OTHER PUBLICATIONS

Cilingiroglu, T.B. et al., "Dictionary-based Image Enhancement for Integrated Circuit Imaging," IEEE International Conference in Acoustics, Speech and Signal Processing (ICASSP), 2013, pp. 1869-1873.

Cilingiroglu, T.B. et al., "Dictionary-based Sparse Representation for Resolution Improvement in Laser Voltage Imaging of CMOS Integrated Circuits," Design, Test and Automation in Europe (2015), 4 pages.

Cilingiroglu, T.B. et al., "Image Reconstruction Techniques for High Numerical Aperture Integrated Circuit Imaging," 38th International Symposium for Testing and Failure Analysis (ISTFA 2012), Phoenix AZ, 6 pages.

Cilingiroglu, T.B., "A Sparsity-based Framework for Resolution Enhancement in Optical Fault Analysis of Integrated Circuits," Ph.D. Disseration, Boston University Theses & Dissertations, Jan. 2015, 222 pages.

Ng, Y.S. et al., "Laser Voltage Imaging: A new Perspective of Laser Voltage Probing," Proceedings from the 36th International Symposium for Testing and Failure Analysis (2010), Addison, TX, USA, 7 pages.

\* cited by examiner

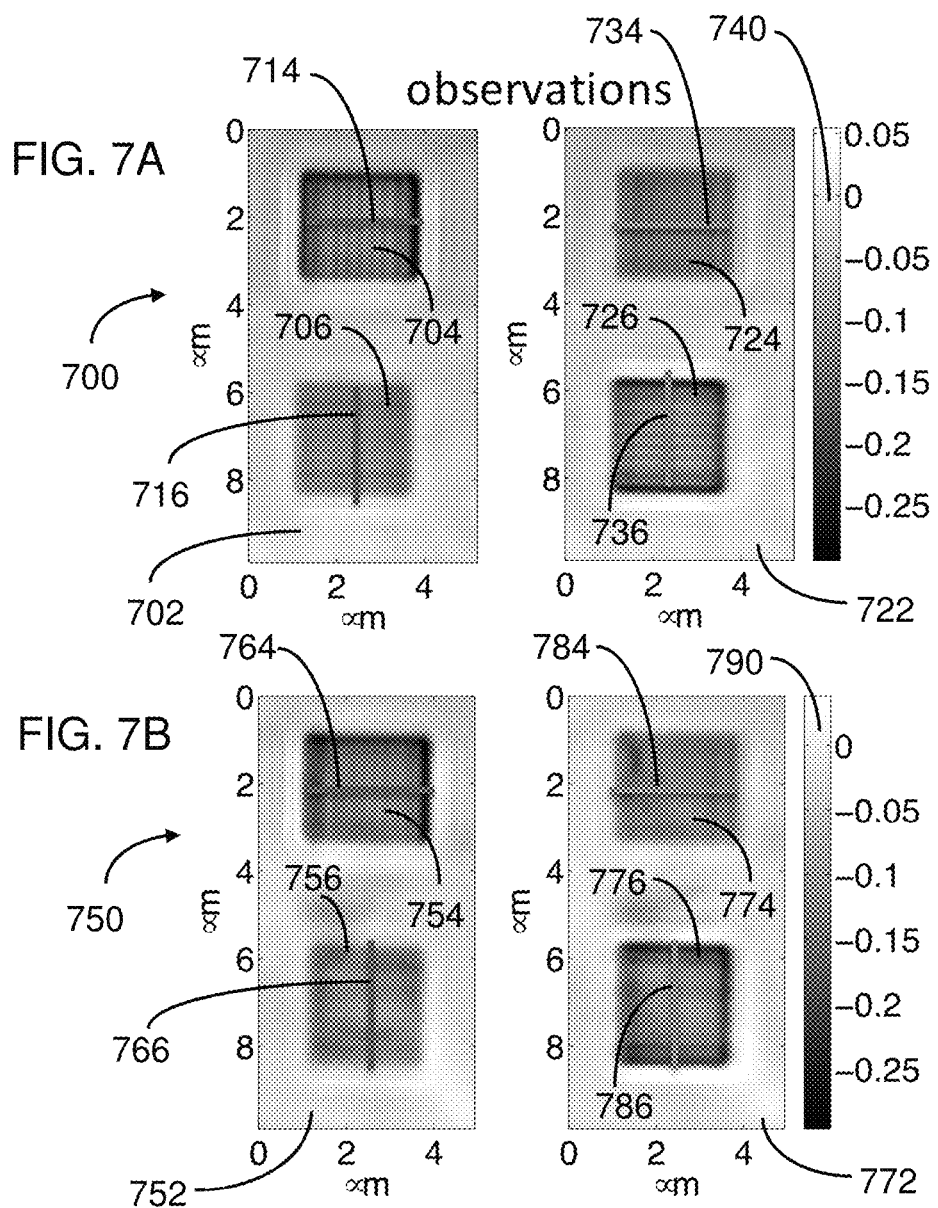

ALIGNMENT OF CAD DATA TO IMAGES IN HIGH RESOLUTION OPTICAL FAULT ANALYSIS

TECHNICAL FIELD OF THE INVENTION

The present invention relates to the field of integrated circuit testing methods, and more specifically to the use of image reconstruction and processing of CAD pattern data to improve the alignment of computer-aided design (CAD) data to images in optical fault analysis.

BACKGROUND OF THE INVENTION

During the design and development of new integrated circuits (ICs), it is necessary to test the performance of these ICs relative to the required specifications. Exemplary optical fault analysis methods include Laser Scanning Microscopy (LSM), Laser Voltage Imaging (LVI) and Laser Voltage Probing (LVP). Optical methods may take advantage of minute (~600 ppm) changes in the reflectivity of conduction regions (e.g., source-gate-drain) arising from voltage-induced changes in carrier concentrations. Some functional testing must be performed on completed ICs, i.e., ICs already having many metal interconnect layers on top of the device layer containing the transistors and other active elements to be tested. Optical imaging for testing or imaging purposes is not possible "looking" through the metal interconnects (the "frontside" of the device) which are opaque to all wavelengths of light. In some applications, optical imaging through the backside of the device ("looking" through the silicon substrate) may require using infrared (IR) light due to the silicon bandgap which causes absorption of light with shorter wavelengths. In other applications, the chip may be backside-thinned to enable the use of shorter wavelengths. In still other applications, alternative methods and wavelengths may be employed to obtain optical images.

As the semiconductor industry has progressed to new device nodes every two to three years, and wherein each node represents about a 30% reduction ($1/\sqrt{2}$ times smaller) in feature sizes, the smallest features on state-of-the-art devices now range to below 20 nm—smaller than the optical resolution achievable with current state-of-the-art optical imaging techniques Typically, a user would like to test, i.e., observe the electrical performance of, various circuit elements within a "sea" of logic defined in a computer-aided design (CAD) database. Typically, the CAD database will contain multiple layers which define the structures within an IC from the substrate to the top of the metal interconnect layers. Backside optical images do not visualize all of these layers, typically only observing the device layer and a few layers above that within the interconnect stack, wherein the imaging of these "higher" layers may be lower contrast or possibly blurred. Usually no fiducial marks are available to aid the alignment of the CAD data to the device image since fiducials would occupy valuable area on the IC which could be better used for devices (maximizing device packing and minimizing the IC size). Thus, the alignment of the CAD data to the device image must usually be performed using the image itself. However due to basic optics considerations, the image resolution may be poorer than the device geometries to be imaged and tested. This makes accurate alignment (registration) between the CAD data and the device image difficult and imprecise. Coarse CAD data-to-image registration may be performed using global alignment of the CAD data to the microscope stage (which itself is aligned to the device). Fine alignment at the nm-level (i.e., smaller than the device geometries) becomes more difficult, and with increasing failure rates, as device continue to shrink with each new device node.

Thus, there is a need for methods to improve the registration precision between the IC CAD data and the optical images to ensure that functional data may be obtained from the exact circuit features of interest, even when surrounded by large numbers of similar features in the IC. As is well known, the CAD data already comprises sharply-defined edges, typically with X- or Y-orientations, surrounding rectangular shapes which may be displayed in either outline or filled-in polygon form. However, the optical images are quite blurry due to resolution limitations of the backside optical imaging systems. To improve CAD data to image registration, it is reasonable to look to methods of image enhancement as a first step towards improving CAD data to image registration.

A pressing need also exists to observe the propagation of electrical signals within the IC under test. This essentially would involve processing of the CAD device pattern data to extract those patterns which are expected to appear in the optical image of the operational device. The processed CAD data may be further improved to demonstrate dynamic behavior when the device is subjected to a pre-determined ac test signal. An example might be the gate and drain voltages of the two transistors within an inverter, surrounded by other transistors which are static (i.e., not switching). Combined with resolution enhancement, a X-Y overlay of the dynamic device structures from the CAD data to the dynamic features on the device under test (DUT) may be accomplished with much higher accuracy.

Another need is to perform probing measurements on DUTs in a much more timely manner than is possible with current LVP methods in which the beam is stationary on part of a device (e.g., a gate) over a period of minutes required to obtain full voltage waveforms. The reason for such lengthy measurement is that the noise amplitude on the acquired periodic signal is too high and it is necessary to collect for a long time and average over the full collection time. During averaging, the signal stays the same but the averaging process decreases the portion of noise in the total signal. Therefore, it is necessary to wait a long time at the stationary probe location. However, when LVI data is acquired, collection is in the frequency domain and the noise is spread across all frequencies.

To optimize the alignment of the CAD data to the optical images, thus it may be beneficial to reconstruct the images and also to process the CAD data to more closely match these reconstructed images.

SUMMARY OF THE INVENTION

An object of the invention is to improve the alignment between the CAD pattern data for a device under test (DUT) with the images acquired during optical fault analysis. This alignment improvement is facilitated by two complementary processes: 1) the use of image reconstruction to improve the image resolution, signal-to-noise, noise level, etc., and 2) processing of the CAD data to more closely resemble the expected optical images (dc and/or ac) to be acquired. By improving the match between the CAD pattern and optical images, substantial improvements in the alignment precision are enabled.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings, in which:

FIG. 7A shows LSM images of the test patterns in FIG. 6A;

FIG. 7B shows LSM images of the test patterns in FIG. 6B;

DETAILED DESCRIPTION OF PREFERRED EMBODIMENTS

Figure 1:
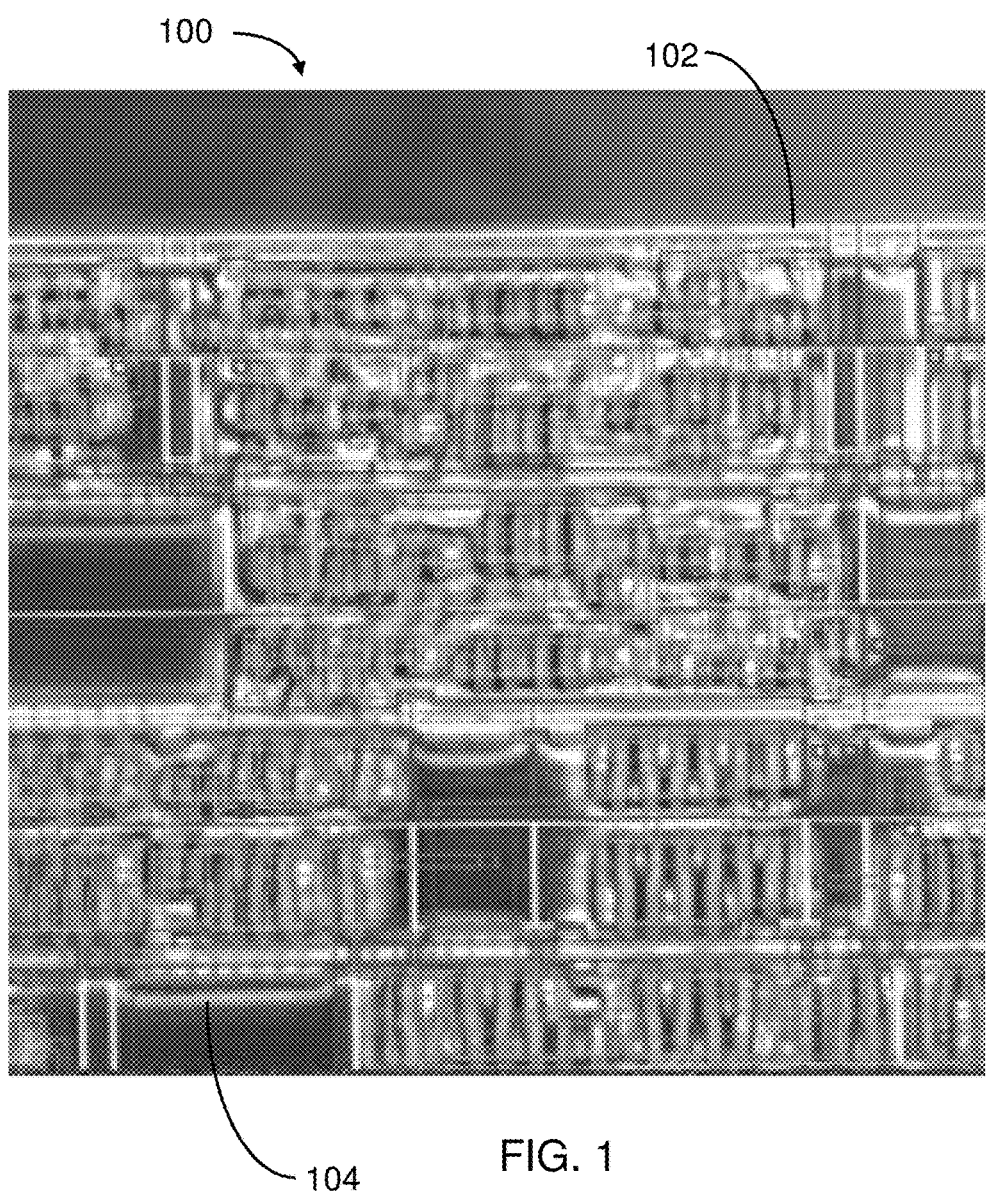
FIG. 1 shows CAD data superimposed on a Laser Scanning Microscope (LSM) image.

Improved alignment between the CAD data for a semiconductor device (IC) under test and an optical image of that device is facilitated by both the use of image reconstruction to improve the resolution, signal-to-noise, noise levels, etc. in the optical images, as well as processing of the CAD pattern data to generate pattern data more representative of the reconstructed optical images.

Many methods for image reconstruction have been developed over several decades for a wide range of imaging applications. These methods comprise multiple objectives for image improvement, including higher resolution, improved signal-to-noise, denoising, etc., which may not be mutually-exclusive. Exemplary methods for image reconstruction will be discussed below, but many other methods also fall within the scope of the invention. Specific image reconstruction techniques are not part of the present invention. Besides the acquisition of static (i.e., dc) images in Laser Scanning Microscopy (LSM), it is also desirable to observe and test the performance of individual transistors or other circuit elements, or groups of transistors (such as a two-transistor inverter), within a much larger number of circuit elements which remain in a static (i.e., non-switching) state.

To facilitate better alignment between the CAD data and the reconstructed images, there may also be a need to process the CAD data to extract patterns for those devices which should be switching under conditions of device operation corresponding to the way that the device is activated (i.e., not all pins may be connected or driven with ac signals) and to exclude patterns for all the other non-switching circuit components. In addition, since the optical images typically only "see" the device layer and possibly a short distance into the interconnect stack, to optimize the correspondence (match) between the reconstructed optical images and the CAD data, it may be preferred to "process" the CAD data to include only those layers expected to appear in the optical images. This processing may comprise various methods for combining the CAD pattern layers, including Boolean functions (AND, OR, XOR, NOT, etc.) between two or more layers, as well as other logical or non-logical functions (see FIG. 3). Specific methods for processing of the CAD data are not part of the present invention.

Registration of the processed CAD data to dynamic optical imaging data acquired using Laser Voltage Imaging (LVI) can enable time-based imaging of devices with the display of both amplitude and phase information which may be compared to the expected dynamic device voltages (on the gate(s) and drain(s) for example). A benefit of reconstructed LVI images with good registration to the processed CAD data is much faster acquisition of ac device performance relative to LVP methods where the laser beam is statically-positioned on a single device to acquire dynamic voltage waveforms over periods of minutes. In LVI methods, since the beam is rastered to acquire many pixels, use of time-slice methods (at various harmonics of the basic driving frequency) enables high signal-to-noise acquisition of device images with both amplitude and phase information out to multiple harmonics of the basic driving frequency of the device.

As described herein, a method for aligning CAD pattern data to an image of a semiconductor device such as an integrated circuit includes receiving CAD data of at least a portion of a semiconductor device, processing this CAD data to select active regions of the device, acquiring Laser Voltage Images with amplitude and/or phase information, applying sparse imaging reconstruction techniques to enhance the resolution of the LVI images, and then aligning the processed CAD data to the enhanced-resolution LVI images.

Also described herein is an alignment system including an image capture module operable to acquire optical images of a semiconductor device, a CAD tool configured to provide CAD pattern data for the semiconductor device, and an alignment tool for: 1) combining one or more CAD pattern data layers to generate a new CAD layer consisting of features which will be active when the device is driven by a particular testing frequency through specified connection pins, 2) applying sparse imaging reconstruction techniques to enhance the resolution of the LVI or LSM images, and then 3) aligning the processed CAD data to the enhanced-resolution images.

Image 100 of FIG. 1 shows CAD data (in outline form) 102 superimposed on a Laser Scanning Microscope (LSM) image 104 in a coarse registration process. The fine and sharp edges of the CAD data are readily apparent as well-known to those skilled in the art. The process of transferring these CAD patterns into the fabrication of all device layers involves a multiplicity of lithographic, etching, deposition, implant, and other processes. For our purposes here, what is important is the patterning fidelity and sharpness of these processes means that the edge sharpness of features in the device layer (and also in the metal interconnect layers above the device layer) closely approximates the shapes in the CAD data, and has very sharp edges beyond the imaging capabilities of an optical system as can be seen from the fuzziness of the LSM image shown here. As described in U.S. Pat. No. 9,064,083 assigned to the Assignee of the present invention, the CAD data is cross-correlated to the LSM image, but this process may not have sufficient precision due to the width of the cross-correlation peak arising from the LSM image blur (see, for example, FIG. 8A in U.S. Pat. No. 9,064,083).

Figure 2A:
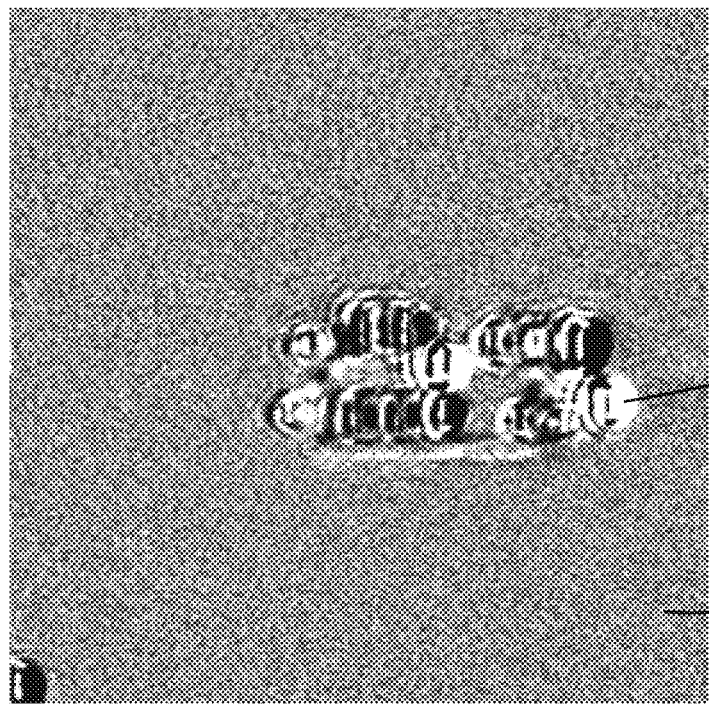
FIG. 2A shows a Laser Voltage Imaging (LVI) phase image.

FIG. 2A shows a Laser Voltage Imaging (LVI) phase image 200, of a device being driven at the inspection frequency. Region 204 represents the majority of the device area which is static and not driven (displayed as an intermediate gray color). Region 202 is being driven and has two phases: largely black and white, but possibly with some grayscale, representing typically gate and drain regions of the FETs under test (the DUTs) at multiple phases.

Figure 2B:
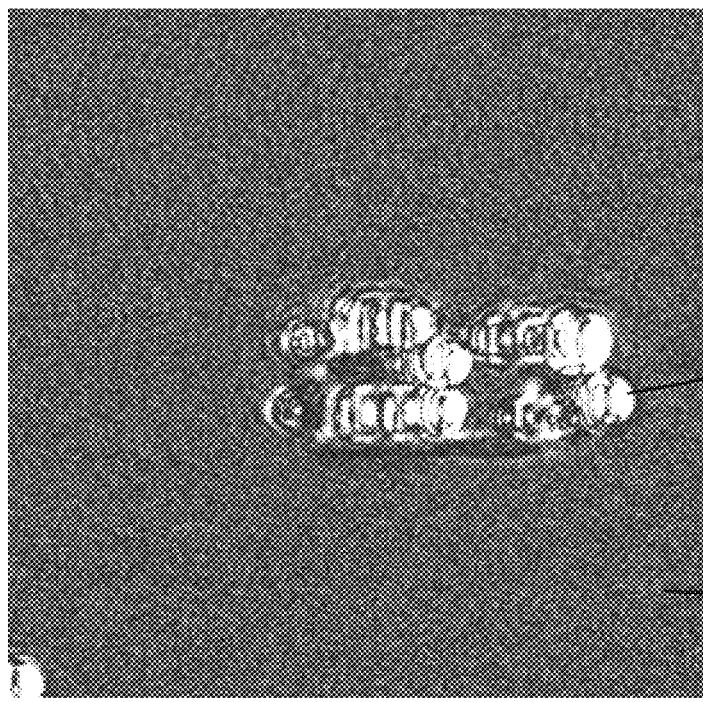
FIG. 2B shows an LVI amplitude image of the region in FIG. 2A.

FIG. 2B shows an LVI amplitude image 250 of the region in FIG. 2A, the amplitude of the regions being driven 252 is shown positive relative to the non-driven regions 254.

Figure 4:
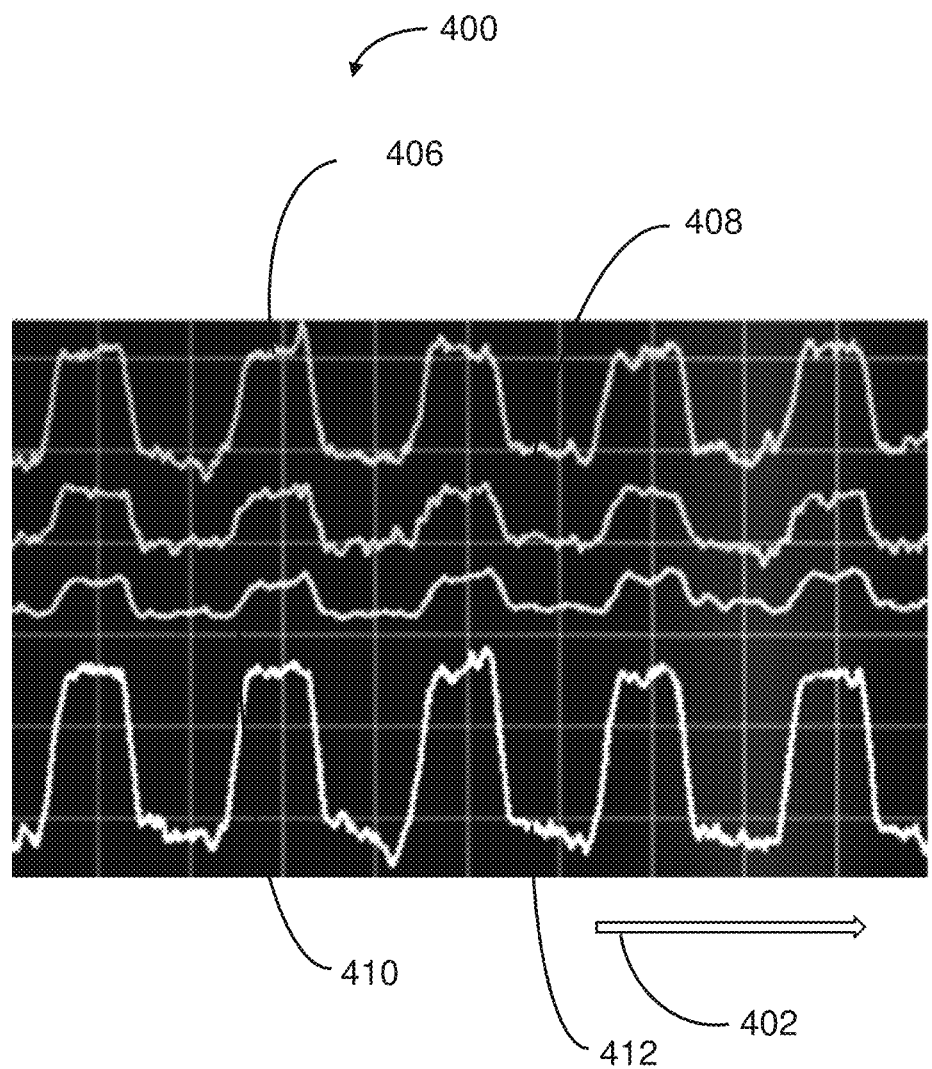
FIG. 4 shows exemplary waveforms in Laser Voltage Probing (LVP)

FIG. 4 shows exemplary waveforms 400 in an example of a typical Laser Voltage Probing (LVP) output display. The time axis 402 is horizontal while the light intensity (correlated to voltage) axis (with separate origins for each of the four curves 406-412) is vertical. Four waveforms 406-412 (in phase with each other in this example, but which could have arbitrary phase relationships in general) are shown here. Noise is clearly visible on the waveforms despite the relatively long (several minutes) acquisition times.

Figure 3:
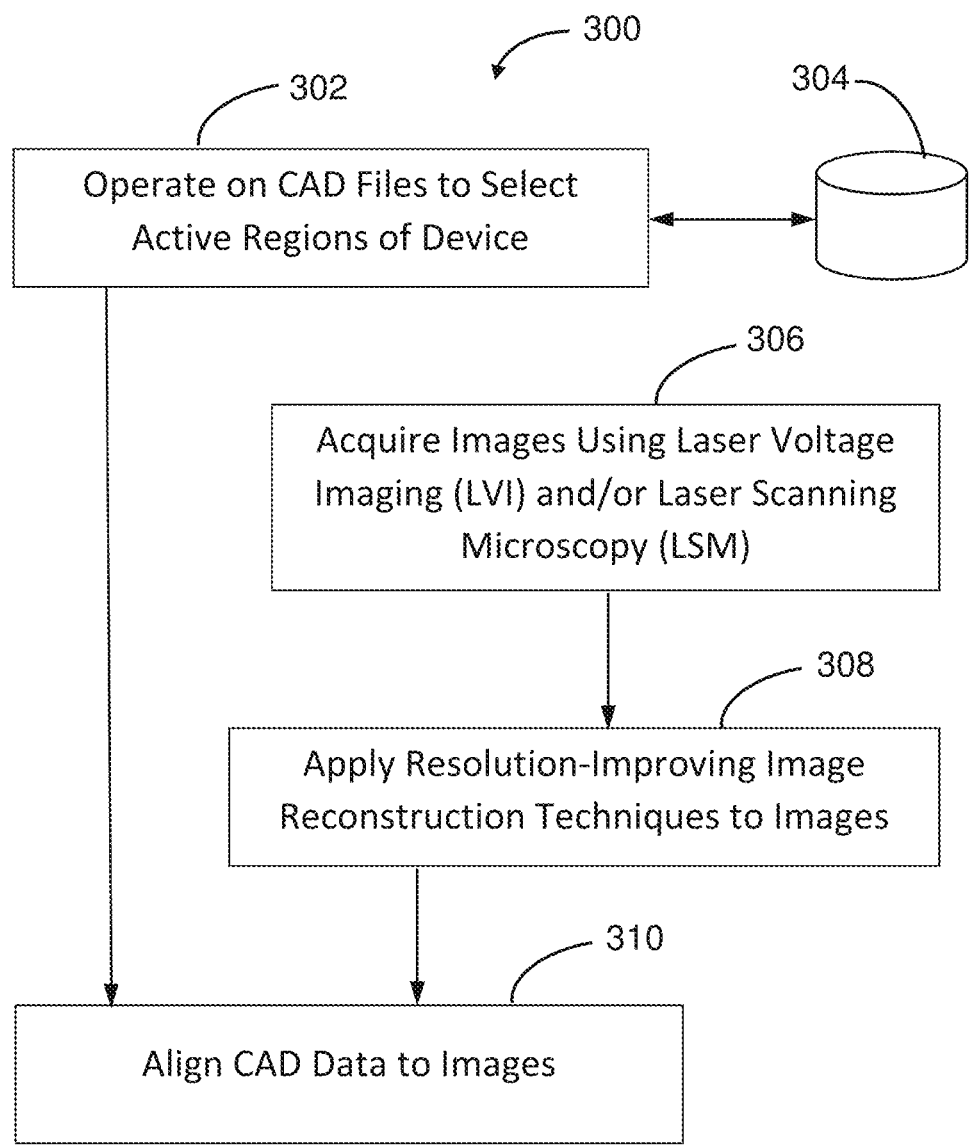
FIG. 3 shows a flowchart of the alignment method of the invention.

FIG. 3 shows a flowchart 300 of an alignment method including both processing of the CAD data as well as image improvement—as discussed above, these two aspects combine to make the "match" between the CAD data and the optical image much closer, thereby facilitating improved alignment between them. CAD data, which may be stored on a non-volatile storage device such as a hard-drive or flash-drive 304, is accessed by an image processing system which may be a general-purpose computer with random-access memory, or a dedicated electronic image processing system employing a microprocessor or FPGA or similar type of computational electronics. Operating either automatically or with operator input, second CAD layers may be generated 302 by processing of one or more CAD pattern data layers. This processing may include various Boolean operations between layers (see FIG. 13), such as AND, OR, XOR, NOT, etc.) as well as other logical or non-logical operations. Processing may also include other operations such as blurring or contrast modification for some pattern layers. The goal of processing is to produce a second CAD pattern layer which more closely matches the expected result of image reconstruction on the first optical images.

Images are acquired 306 typically using backside optical imaging often employing high numerical aperture optics such as a Solid Immersion Lens (SIL) to obtain the best-possible resolution taking into account that the wavelength is larger than the device feature sizes. These LVI images (amplitude and/or phase) are then resolution-enhanced 308 to reveal features which may be difficult or even impossible to see in the original optical images—as a result of this resolution enhancement, the images now look similar to the CAD pattern data if it is displayed in filled-in polygon form. Finally, in block 310 the CAD layers from block 302 are aligned to the images from block 308. The results of this alignment are illustrated in FIG. 18B, showing the CAD data superimposed on an LSM image.

Figure 5:
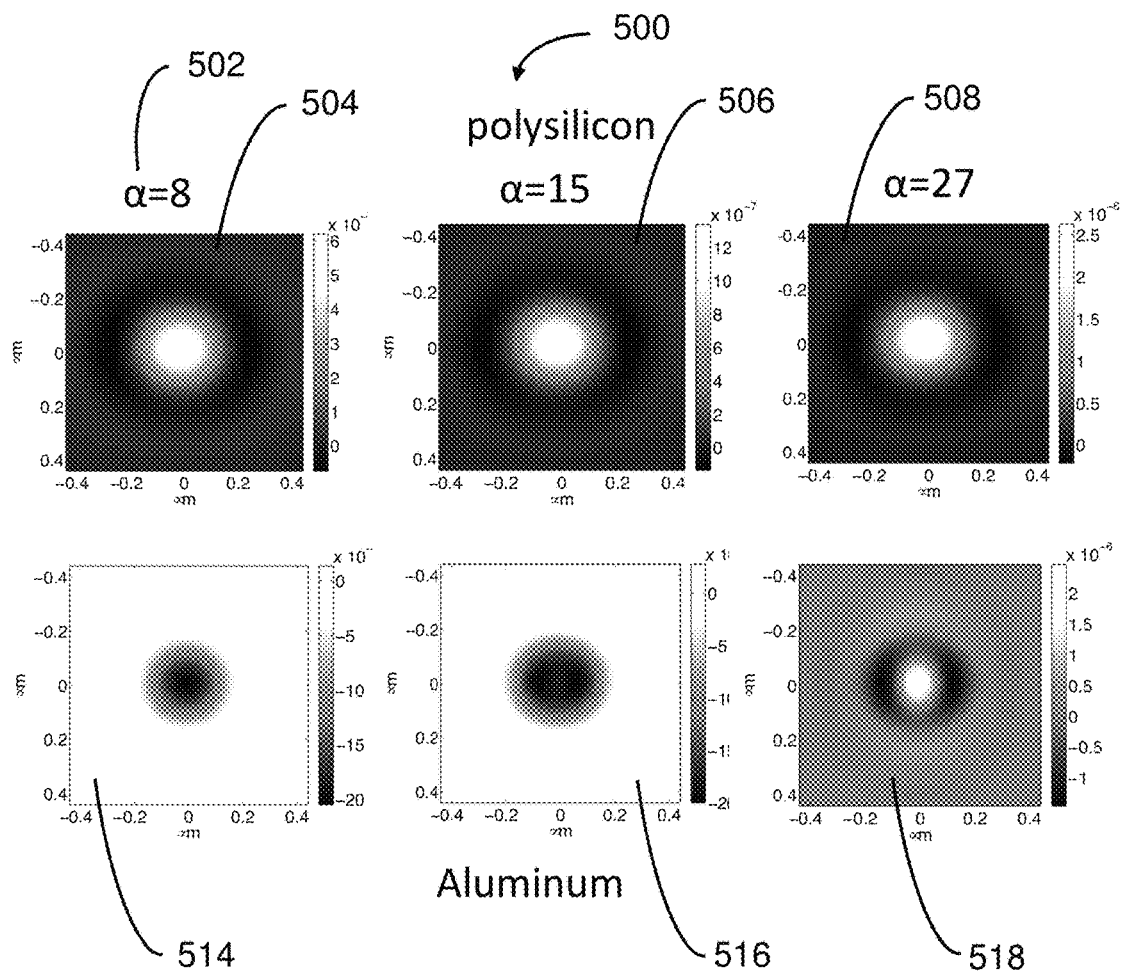
FIG. 5 shows Point Spread Functions (PSFs) for three sizes of polysilicon and aluminum objects.

FIG. 5 shows Point Spread Functions (PSFs) 500 for three sizes 502, 506, and 508 of polysilicon test objects, and of three sizes 514, 516, and 518 of aluminum test objects. The following is one of many possible formulations for the PSFs. The PSF may be modeled and simulated differently, using different theories. Also, the PSF may be estimated from experimental data instead of a theoretical simulation. Details of methods for formulating the PSF are known.

In some embodiments, polysilicon structures are fabricated at a silicon-to-silicon dioxide interface. The aluminum structures are fabricated on the surface of a double-sided polished wafer and thus are at a silicon-to-air interface. The parameter a is proportional to the scattering strength of each feature which theory indicates should scale with (dimension)$^3$—thus the three values of $\alpha$ correspond to $2^3$, $2.5^3$, and $3^3$. As can be seen from images 504, 506, and 508, the PSF does not change substantially as $\alpha$ is increased. Conversely, images 514, 516, and 518 show that the PSFs for aluminum on silicon change much more dramatically as $\alpha$ is increased. For all six images, the light is vertically polarized (Y-axis).

The following formula expresses the calculation of the PSF h(x,y):

$$h(x,y) = \|\alpha * \bar{\bar{G}}_{SIL}(x,y;x',y') * \vec{E}_{Scatt}(x',y') + \vec{E}_{Ref}(x,y)\| - \|\vec{E}_{Ref}(x,y)\|^2,$$

Where

α is as described above, a coefficient accounting for the increase in the scattered field as the size of the scattering object is increased, $G_{SIL}$ (x, y; x', y') is the Green's function for scattering at (x', y') to an image at (x, y). The subscript SIL corresponds to imaging with a Solid Immersion Lens as is commonly used for LSM, LVI and LVP testing.

x and y are coordinates in the image plane (where the PSF is observed), x' and y' are coordinates in the object plane (where the object is scattering light), $E_{Scatt}$ is the electric field due to scattering from the object, and $E_{Ref}$ is the electric field due to light reflected from the interface supporting the scattering object.

Figure 6A:
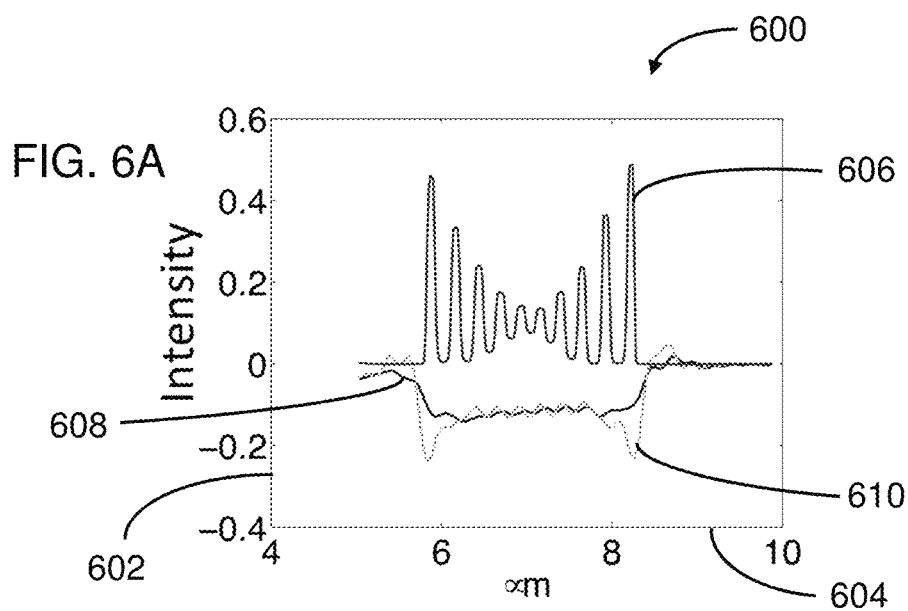
FIG. 6A shows intensity profiles for Laser Scanning Microscope (LSM) images of test patterns with 252 nm line spacings and two polarization directions, as well as profiles from higher resolution reconstructions.
Figure 6B:
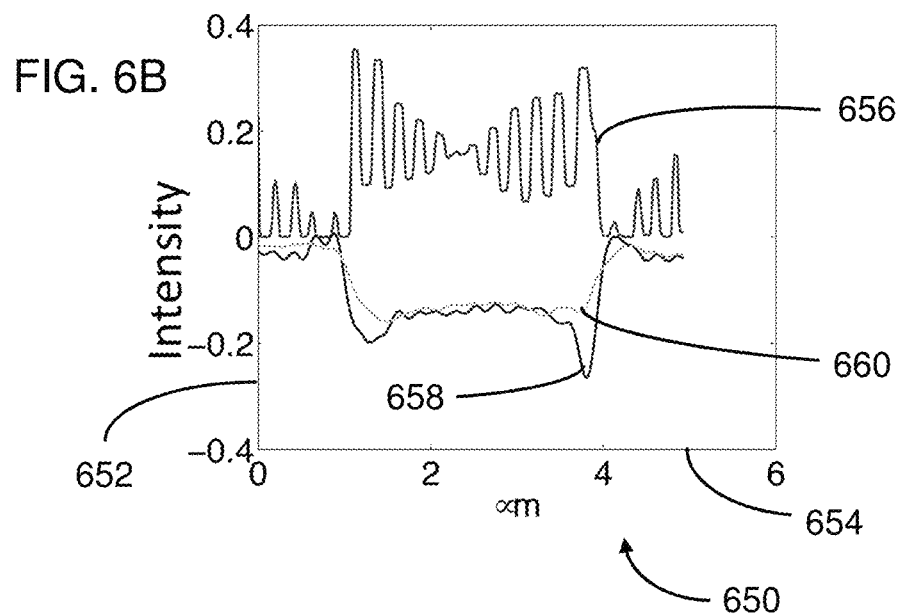
FIG. 6B shows intensity profiles for Laser Scanning Microscope (LSM) images of test patterns with 224 nm line spacings and two polarization directions, as well as profiles from higher resolution reconstructions.

FIGS. 6A and 6B show intensity profiles 600 and 650, respectively, for Laser Scanning Microscope (LSM) images of test patterns comprising multiplicities of horizontal Aluminum lines with two different spacings. Profile 600 in FIG. 6A corresponds to line spacings of 252 nm, where the intensity 602 is graphed relative to position 604. Curve 608 is for x-axis polarization (horizontal—line 716 in FIG. 7A) and curve 610 is for y-axis polarization (line 736 in FIG. 7A). For both curves 608 and 610, the signal-to-noise is clearly very weak. Curve 606 (line 816 in FIG. 8A) represents the reconstruction of the horizontal lines, clearly with much-improved intensity and sharper edges. Profile 650 in FIG. 6B corresponds to line spacings of 224 nm, where the intensity 652 is graphed relative to position 654. Curve 658 is for x-axis polarization (horizontal—line 766 in FIG. 7B) and curve 660 is for y-axis polarization (line 786 in FIG. 7B). For both curves 658 and 660, the signal-to-noise is clearly even weaker than for curves 608 and 610 since the Solid Immersion Lens cannot resolve these finer lines. Curve 656 (line 866 in FIG. 8B) represents the reconstruction of the horizontal lines, again clearly with much-improved intensity and sharper edges.

FIGS. 7A and 7B show LSM images 700 and 750 of the test patterns in FIGS. 6A and 6B, respectively. In FIG. 7A are four images of the test structure comprising multiple Aluminum lines spaced 252 nm and oriented both horizontally and vertically, and imaged with light polarized horizontally and vertically. Grayscale 740 illustrates the intensity scale for FIG. 7A. Images 702 have horizontal polarization while images 722 have vertical polarization. Images 704 and 724 have vertical Al lines, while images 706 and 726 have horizontal Al lines. Lines 714, 716, 734 and 736 are perpendicular to the orientations of the Al lines and correspond to the data acquisition scan axes, as shown in FIG. 6A. In FIG. 7B are four images of the test structure comprising multiple Aluminum lines spaced 224 nm and oriented both horizontally and vertically, and imaged with light polarized horizontally and vertically. Grayscale 790 illustrates the intensity scale for FIG. 7B. Images 752 have horizontal polarization while images 772 have vertical polarization. Images 754 and 774 have vertical Al lines, while images 756 and 776 have horizontal Al lines. Lines 764, 766, 784 and 786 are perpendicular to the orientations of the Al lines and correspond to the data acquisition scan axes, as shown in FIG. 6B. Note that for these more closely spaced lines, it is very difficult to distinguish the lines.

Figure 8A:
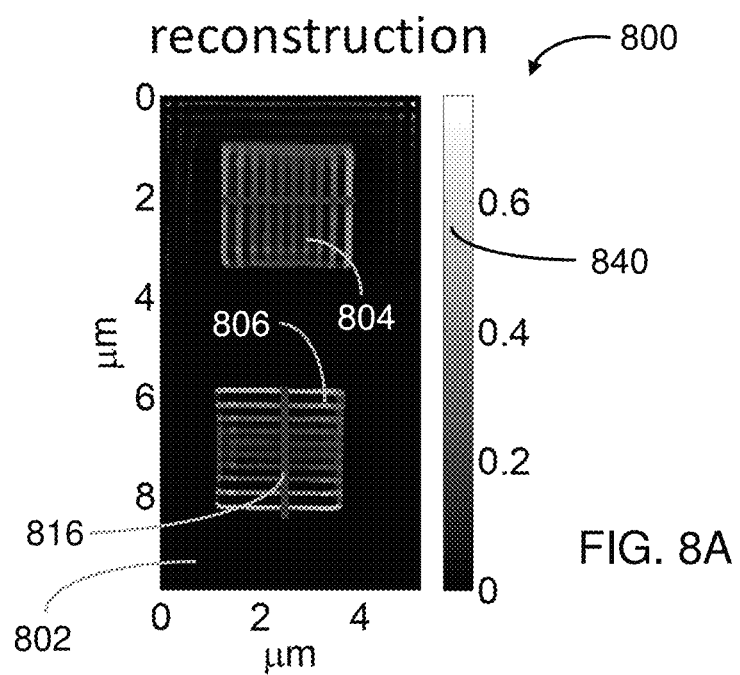
FIG. 8A shows reconstructed images of the test patterns in FIG. 7A.
Figure 8B:
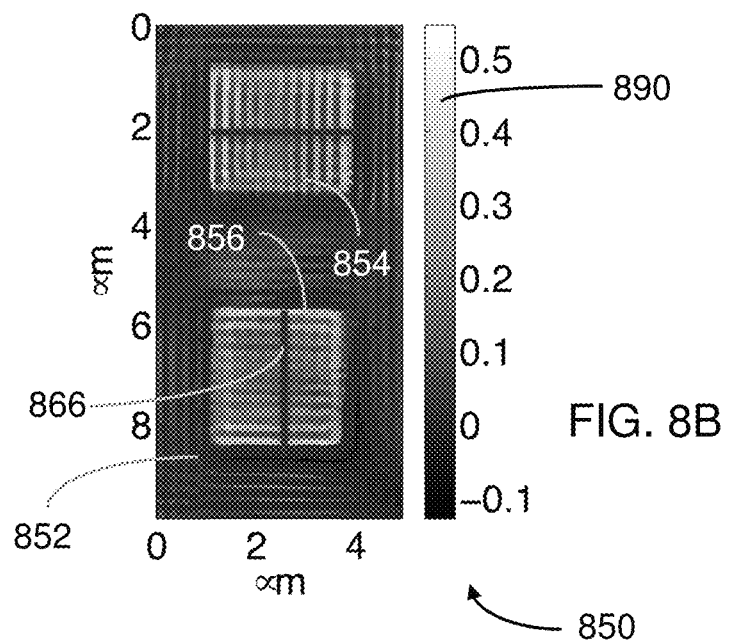
FIG. 8B shows reconstructed images of the test patterns in FIG. 7B.

FIGS. 8A and 8B show reconstructed images of the test patterns in FIGS. 7A and 7B, respectively. In FIG. 8A, two reconstructions 802 are shown for vertical 804 and horizontal 806 lines with 252 nm spacings. The image intensity along line 816 is graphed as curve 606 in FIG. 6A—note the substantial increase in resolution achieved by the reconstruction process outlined below. In FIG. 8B, two reconstructions 852 are shown for vertical 854 and horizontal 856 lines with 224 nm spacings. The image intensity along line 866 is graphed as curve 656 in FIG. 6B—note the substantial increase in resolution achieved by the reconstruction process outlined below. Grayscales 840 and 890 show intensities for images 800 and 850, respectively.

This section discusses some exemplary image reconstruction methods. The invention is not limited to using any specific reconstruction method. Image reconstruction comprises various methods for processing initial images, such as images acquired using a Solid Immersion Lens (SIL) as is commonly used for LSM and LVI device imaging. The process of image reconstruction often employs "regularization" as is familiar to those skilled in the art. Details of these methods are provided in the *Handbook of Image and Video Processing*, "Chapter 3: Regularization in Image Restoration and Reconstruction", by W. Clem Karl. Further information is provided in: Cetin, M., Stojanovic, I., Onhon, N., Varshney, K., Samadi, S., Karl, W., and Willsky, A. (2014). "Sparsity-driven synthetic aperture radar imaging: Reconstruction, autofocusing, moving targets, and compressed sensing". IEEE Signal Processing Magazine, 31(4):27-40.

Figure 9A:
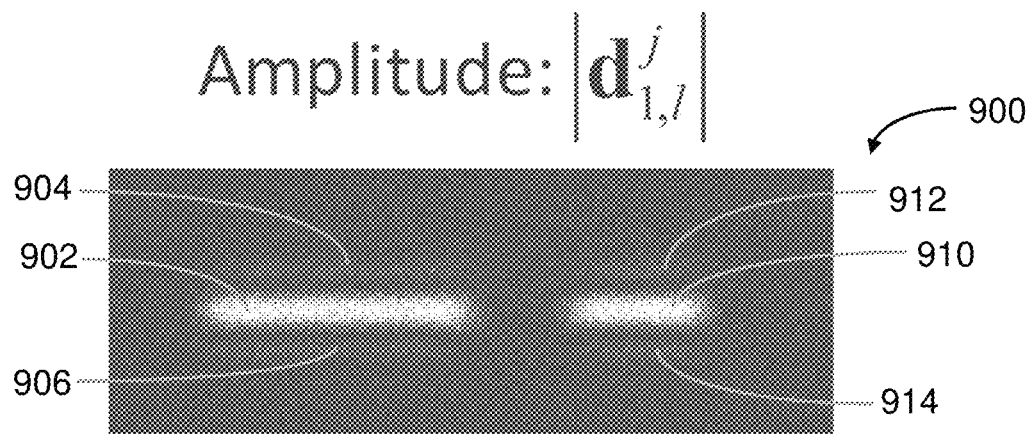
FIG. 9A shows an amplitude LVI image of an inverter.
Figure 9B:
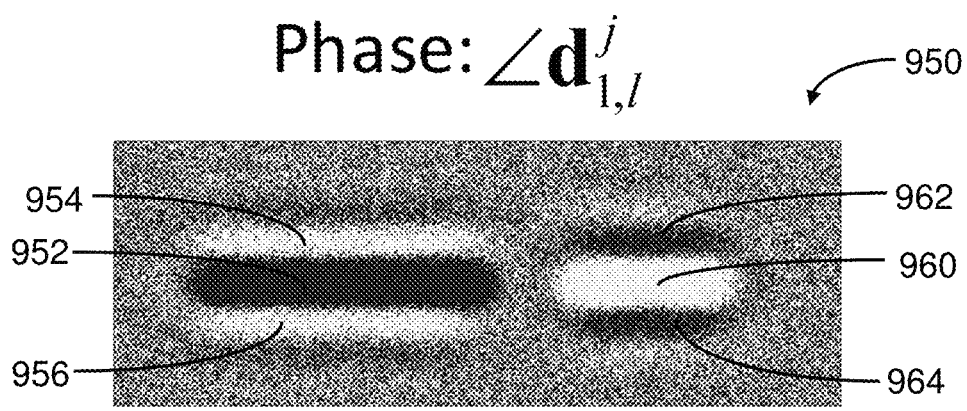
FIG. 9B shows a phase LVI image of the inverter in FIG. 9A.
Figure 9C:
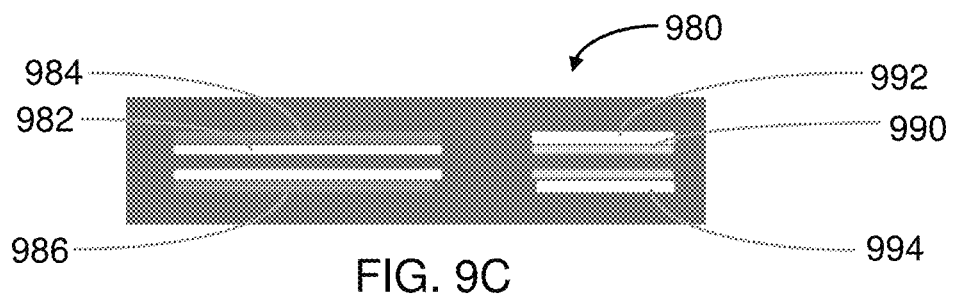
FIG. 9C shows a CAD layout of the inverter in FIG. 9A.

FIG. 9A shows amplitude 900, and FIG. 9B shows phase 950, LVI simulated images of an inverter being driven at the inspection frequency. Also shown is a CAD layout FIG. 9C of the inverter. The inverter comprises a PMOSFET at the left and an NMOSFET at the right. The PMOSFET is slightly longer than the NMOSFET as can be seen in the CAD layout 980 in FIG. 9C—this is due to well-known fabrication issues. In FIG. 9A the centers 902 and 910 are blurred amplitude images of the PMOS gate 982 and NMOS gate 990, respectively, both of which are driven at the inspection frequency (the $1^{st}$-harmonic). Above and below gate image 902 are the drain images 904 and 906, corresponding to drains 984 and 986 in CAD pattern 980. Similarly, above and below gate image 910 are the drain images 912 and 914, corresponding to drains 992 and 994 in CAD pattern 980. In FIG. 9B the PMOS gate 952 can be seen to have the opposite phase from the NMOS gate 960. Similarly, the PMOS drains 954 and 956 have the opposite phase as the PMOS gate 952, and the NMOS drains 962 and 964 have the opposite phase as the NMOS gate 960—this is consistent with the known operating modes of MOSFETs. Note that due to the imaging resolution in both FIGS. 9A and 9B being lower than the feature sizes of the transistors FIG. 9C, the two gates 982 blur together to produce image features 902 and 952 in FIGS. 9A and 9B, respectively. Similarly, the two gates 990 blur together to produce image features 910 and 960 in FIGS. 9A and 9B, respectively. The sources for the two transistors in this invertor are between the two gates for the two transistors and are not driven—thus they do not appear in the processed CAD pattern in FIG. 9C which only shows features which vary in voltage at the driving frequency. Since the driving frequency is a square wave with a 50% duty cycle, in general the frequency components will be largely odd harmonics with decreasing amplitudes. Images 900 and 950 are simulated using PSF 516 in FIG. 5. Methods for modeling PSFs are known to those skilled in the art. Images 900 and 950 have had noise added, with a Gaussian dependence based on the combined dc+ac signal strength (using the standard √N assumption).

Following the step of convoluting the CAD data for the inverter with the PSF to produce FIGS. 9A and 9B, followed by the addition of statistical noise, a deconvolution was applied to each harmonic image from the 1$^{st}$ to the 5$^{th}$ harmonic of the driving frequency using $l_1$ regularization (non-quadratic). Those skilled in the art will be familiar with image processing utilizing $l_1$ regularization which has advantages over $l_2$ (Tikhonov, quadratic, or least-squares) regularization in being less sensitive to noise in the image. The result of this step will be the generation of higher-resolution images [complex, i.e., with both amplitude and phase information] at each harmonic of the driving frequency.

A Fourier series expansion of this data can also be generated to simulate LVP data:

$$\hat{\tau}_k^j(t) = \sum_{l=1}^{5} 2|\hat{d}_{k,l}^j|\cos(lw_o t + <\hat{d}_{k,l}^j)$$

Where
$\hat{\tau}_k^j(t)$ is the time domain representation
and the indices indicate:
  k is the scan position (on an X-Y imaging raster),
  l is the harmonic of the driving frequency (1, 2, . . . ),
  j is the light polarization direction index, and
  $w_0$ is the driving frequency.

Other resolution improvement methods include dictionary-based methods have been shown to exceed the performance of $l_p$ (p≤2) regularization techniques. For these methods, regularization employs a "dictionary" comprising large numbers of shapes typical of those found in the CAD data. Typically, this will comprise rectangles with various widths and lengths, oriented along the X- and Y-axes. Regularization employing these dictionaries thus makes maximum use of pre-defined knowledge about the patterns which should exist on the device (we assume that either there are no patterning errors, or that they can be added to the dictionary).

The preceding discussion has emphasized methods in which the device under test (DUT) is illuminated by a laser, either in a scanned raster (as in LVI) or in a stationary location (LVP), but the invention is not limited to such methods. For example, in some embodiments, the DUT emits light which is detected using a high quantum efficacy IR camera, that is generally cooled (LN$_2$) allowing for detection of "hot carrier emission". In this method, an emission image is acquired by taking two images: a first image where the device is not powered (a "background"), and a second image of the same field of view, with the device powered on. The two images are subtracted, displaying the final "hot carrier emission" data. Similarly to an LVI image, the final emission image will only depict sites where the transistors are active and we are able to apply the same logic to provide a superior alignment.

Figure 10A:
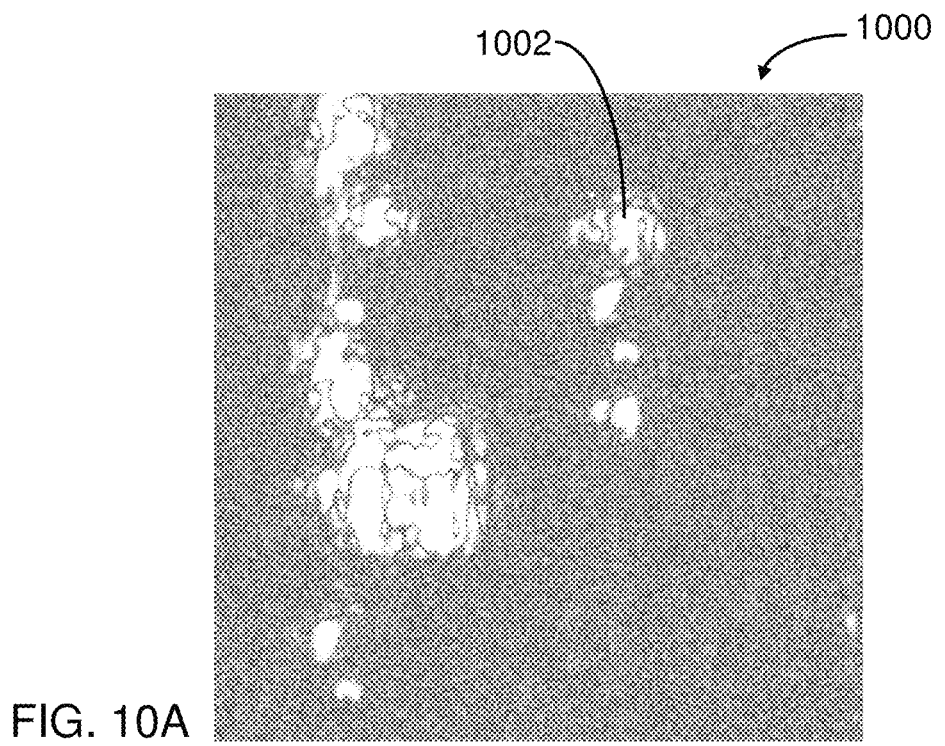
FIG. 10A shows an LVI $1^{st}$-harmonic amplitude image.
Figure 10B:
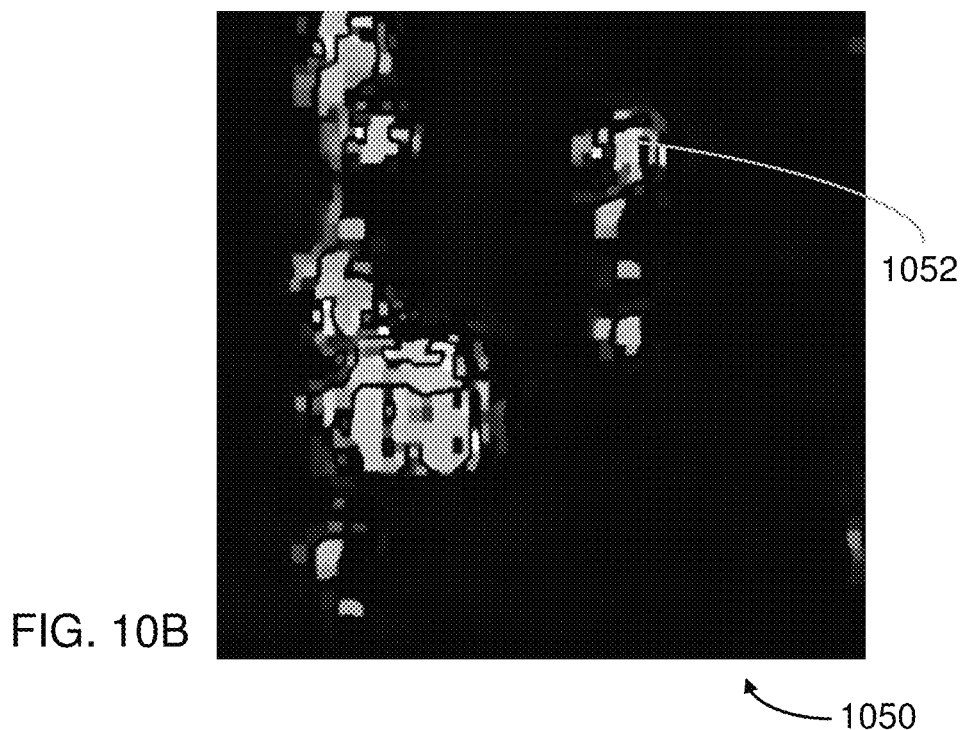
FIG. 10B shows a higher-resolution reconstruction from the LVI $1^{st}$-harmonic amplitude image in FIG. 10A.

FIG. 10A shows an LVI Pt-harmonic amplitude image 1000 and FIG. 10B shows a higher-resolution amplitude image reconstruction 1050. Areas of the device being driven at the inspection frequency 1002 appear white in 1000, against a noisy gray background representing static areas of the device. In this particular example, $l_1$ regularization was used to produce the sharper image in FIG. 10B. Areas 1052 in FIG. 10B correspond to sharpened images of areas 1002 in FIG. 10A. Clearly the image in FIG. 10B more closely approximates the black/white two-level characteristics of the initial device CAD data. In this example, the 1$^{st}$-harmonic data was used. Data for higher odd harmonics (3$^{rd}$, 5$^{th}$, etc.) will be similar but with less intensity. Data for higher even harmonics, at least in the case of 50% duty cycle square-wave modulation, will be very weak or non-existent.

Figure 11A:
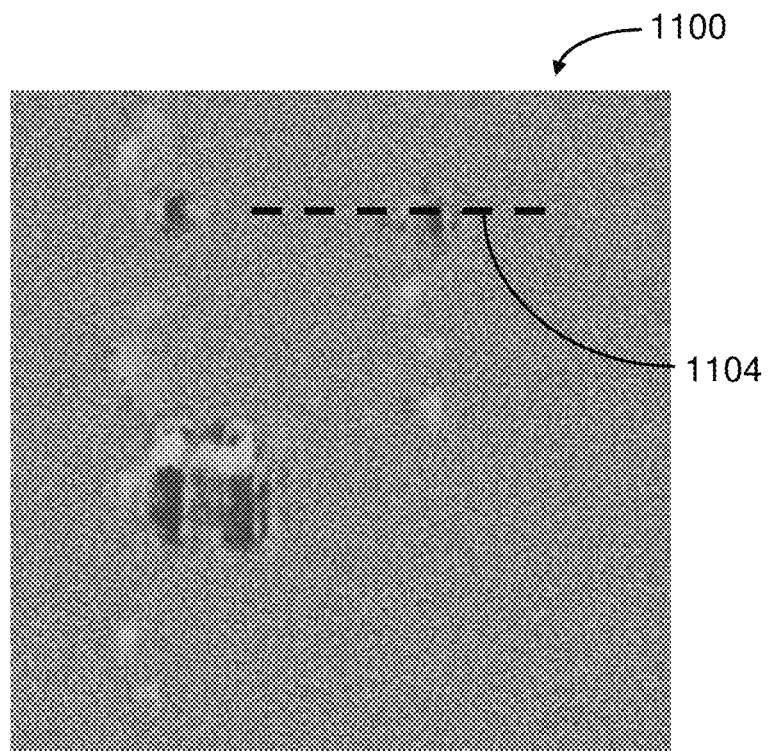
FIG. 11A shows an LVI $1^{st}$-harmonic phase image.
Figure 11B:
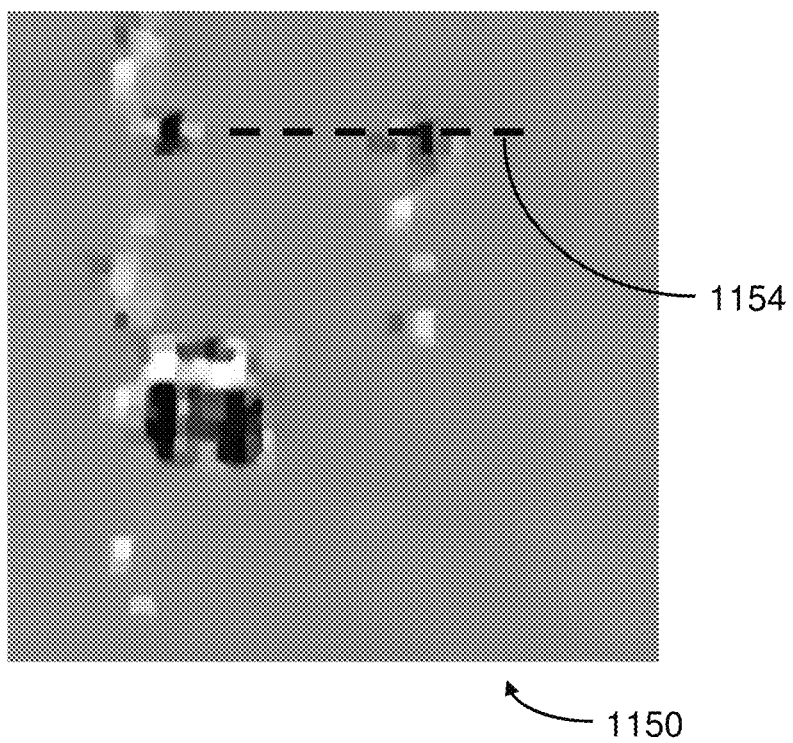
FIG. 11B shows a higher-resolution reconstruction from the LVI $1^{st}$-harmonic phase image in FIG. 11A.

FIG. 11A shows an LVI 1$^{st}$-harmonic phase image 1100 and in FIG. 11B a higher-resolution phase image reconstruction 1150 of the same regions of the device as were shown in FIGS. 10A and 10B, respectively. As was seen in FIG. 9B, the phase image demonstrates multiple intensities: some intensities primarily for driven regions, and some intensities corresponding to static (i.e., non-driven) areas of the device. The dashed lines 1104 and 1154 apply to FIG. 12.

Figure 12:
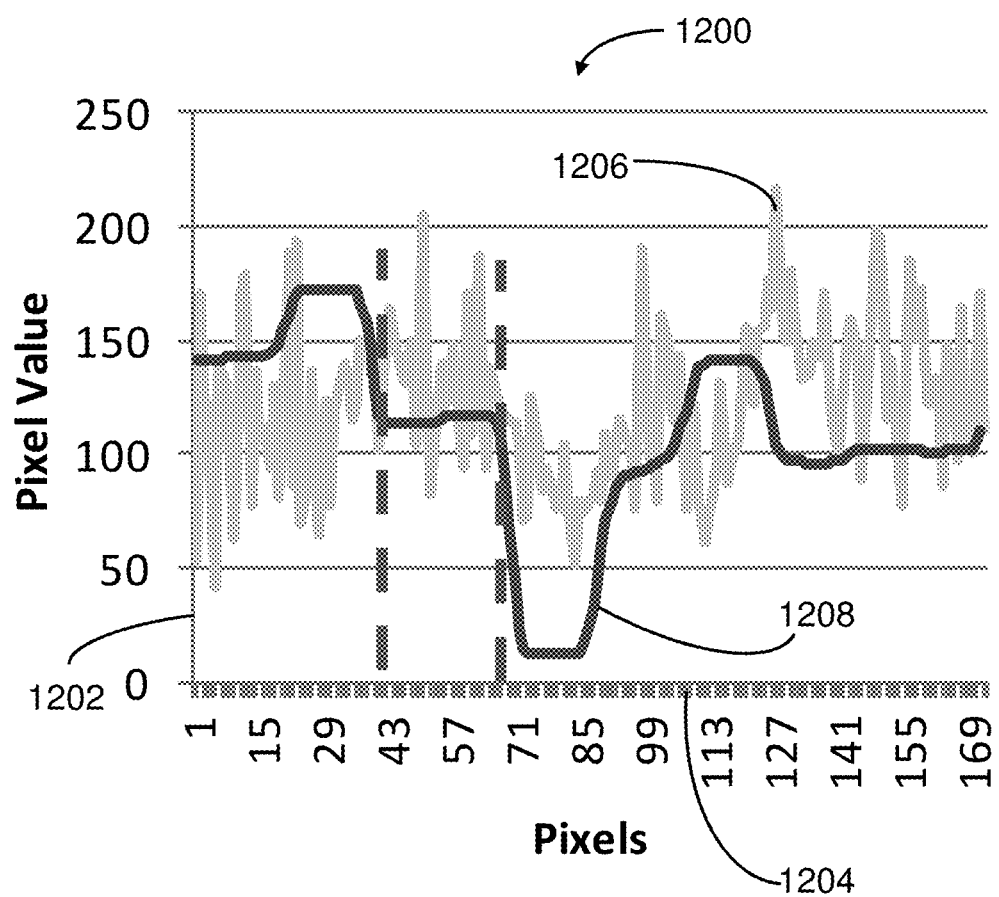
FIG. 12 shows pixel values along the dashed lines in FIGS. 11A-11B for the LVI phase image and the reconstruction.

FIG. 12 shows 1200 pixel values 1202 against the pixel number 1204. Highly noisy curve 1206 plots pixel values along line 1104 through a driven area of the device as shown in FIG. 11A. Note that the noise amplitude rivals the amplitude of the phase image data from the device, thus registering this un-enhanced image to the CAD data would be difficult or at least highly inaccurate. Smooth curve 1208 plots pixel values along line 1154 through the same areas as for curve 1206. The three levels are clearly visible and registering this enhanced image to the CAD data should be highly precise in comparison with the prior art methods represented in curve 1206

Figure 13:
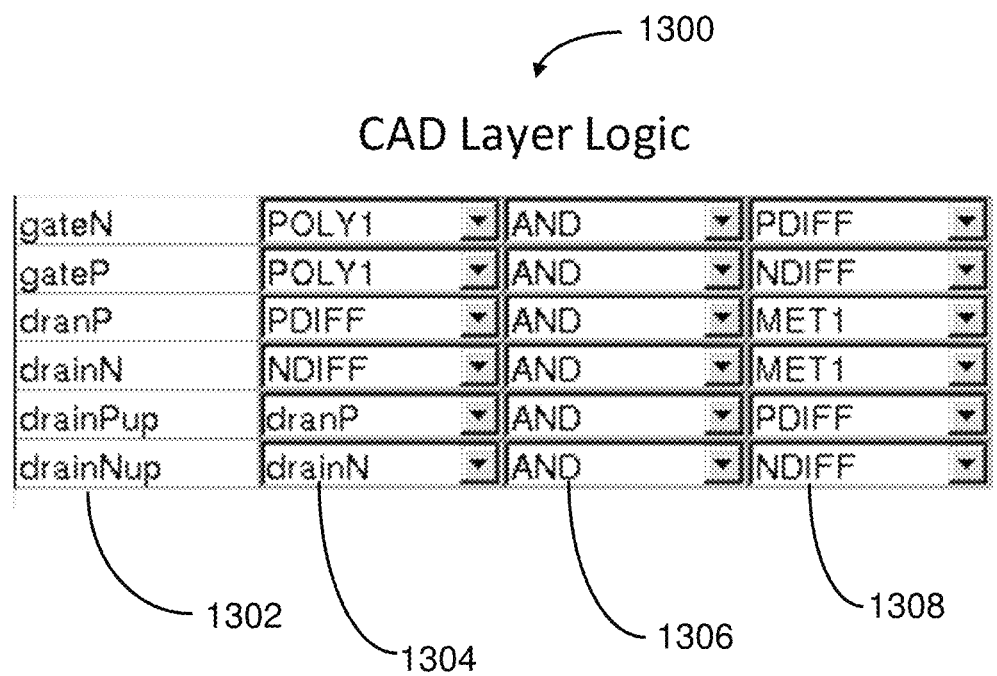
FIG. 13 shows the on-screen data-selection table for generating specific CAD layers relevant to the LVI data source.

FIG. 13 shows 1300 an on-screen data-selection table for generating specific CAD layers relevant to the LVI data source. Column 1302 at the left represents pre-defined layer labels, such as for N-type gates, P-type gates, etc. Columns 1304 and 1308 represent available choices of CAD data layers which may then be combined with the selectable Boolean operators in column 1306. For example, the p-type DRAIN layer ("drainP") would be defined by:

drainP=(PDIFF) AND (MET1).

U.S. Pat. No. 9,064,083 assigned to the Assignee of the present invention, discloses a method of finding transistor and diode regions. Some embodiments can go beyond this to identify sub-regions within transistors such as sources, gates and drains and to then isolate which sources, gates and drains may be active when the device is driven by a particular inspection frequency on specific pins. These sub-regions of specific transistors should then be (in a non-defective device) the regions which will provide the LVI and LVP signals.

The operation in block 302 of FIG. 3 may comprise a number of non-mutually exclusive options:

1. Boolean logic operations, such as AND, OR, XOR, NOT, etc, between one or more CAD layers. This may be useful to simulate the penetration of light through various layers within the device layer (e.g., source, drain, gate, etc.) and in some cases into a few layers at the bottom of the interconnect stack.

2. Modification to one or more layers of the contrast and/or brightness. This may be useful to "simulate" the attenuation of the light from some layers, relative to the device layer.

3. Modification to one or more layers of the sharpness or blurriness. This may be useful to "simulate" the scattering of the light from some layers, relative to the device layer.

Figure 14A:
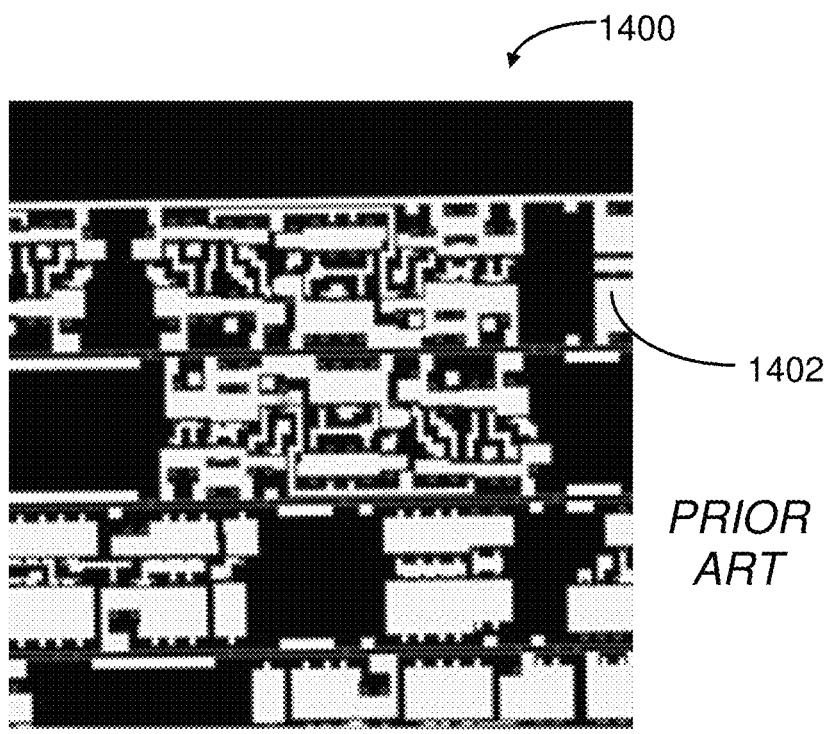
FIG. 14A shows full CAD data in a prior art failed attempt at aligning CAD data to an LVI image.
Figure 14B:
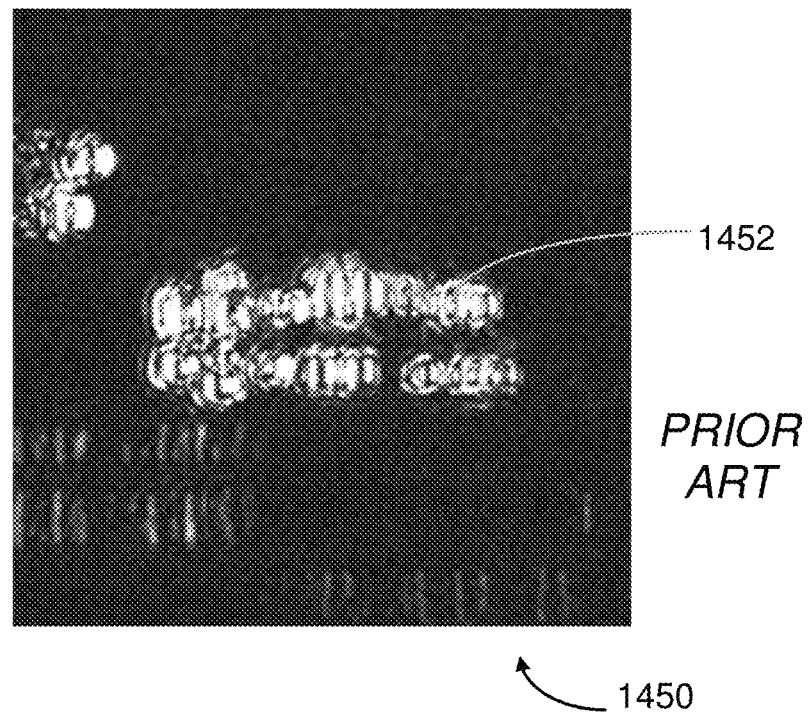
FIG. 14B shows LVI amplitude data in a prior art failed attempt at aligning CAD data to an LVI image.

FIGS. 14A and 14B show a prior art failed attempt at aligning CAD data 1400 to an LVI image 1450. The CAD data 1402 in FIG. 14A is shown in filled-in polygon form where the white areas represent structures on the device. The LVI amplitude data in FIG. 14B shows both driven regions (mostly white and black with some grayscale) 1452 and static regions (dark gray). Registration between CAD data 1400 and LVI image 1450 can be seen to be difficult due to the substantial difference in appearance between the rectangular CAD data with sharp edges and square corners and the rounded gray-level LVI image 1450. Registration is also difficult because the full CAD data is more crowded since it also shows (non-driven) regions where there is no LVI data.

Figure 15A:
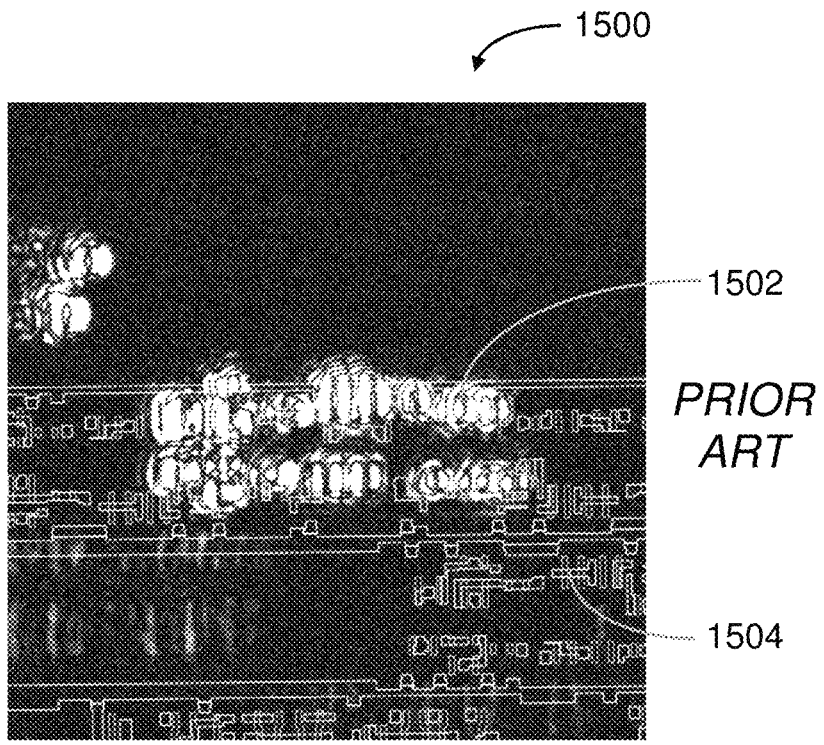
FIG. 15A shows CAD data overlaid on an amplitude LVI image from the failed prior art alignment attempt in FIGS. 14A-14B.
Figure 15B:
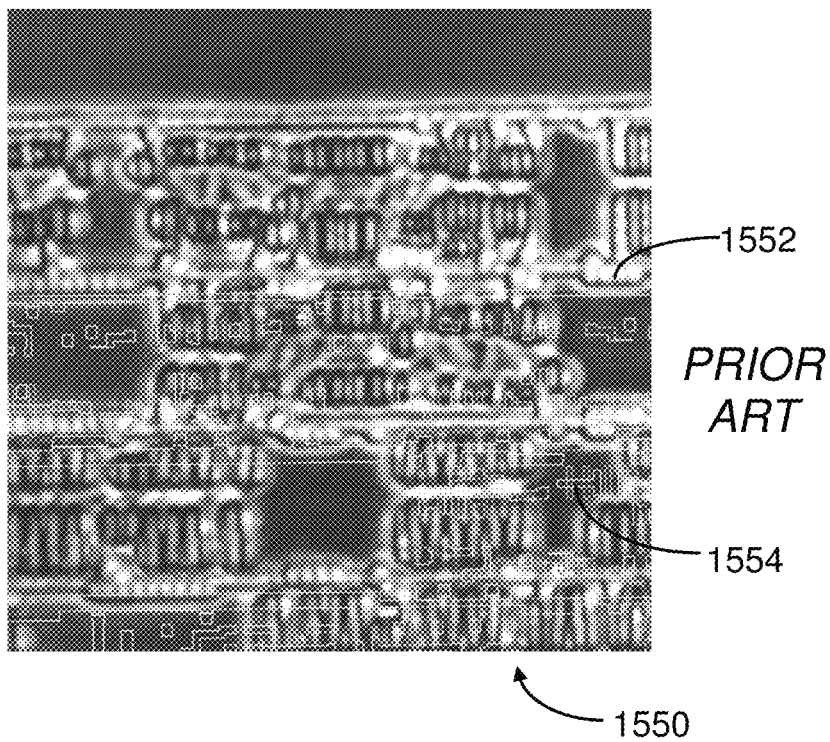
FIG. 15B shows CAD data overlaid on an LSM image from the failed prior art alignment attempt in FIGS. 14A-14B.

FIG. 15A 1500 shows the CAD data 1400 and FIG. 15B shows an LVI image 1450 from FIG. 14B overlaid on each other, although here the CAD data is displayed in outline form (not filled-in polygon form). Complete misalignment of the two patterns may be seen by the lack of correlation between the CAD data 1504 and the LVI image features 1502, thus the registration procedure has failed in this prior art example. Although FIG. 15A shows the CAD data as outlines, correlation is performed using filled-in polygons. FIG. 15B 1550 shows the same calculated registration X-Y offsets as in FIG. 15A, but here the CAD data 1554 is overlaid on the LSM image 1552 which shows more layers and structures of the DUT.

Figure 16A:
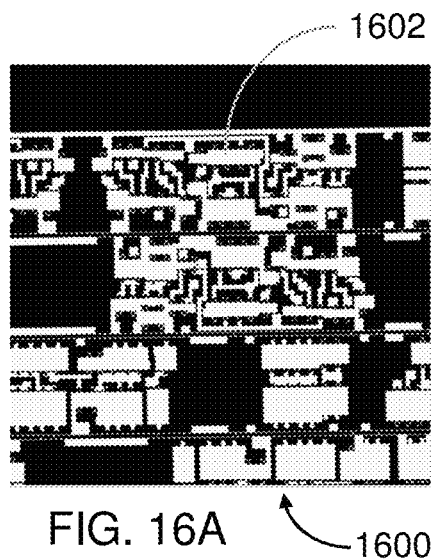
FIG. 16A shows full CAD data.
Figure 16B:
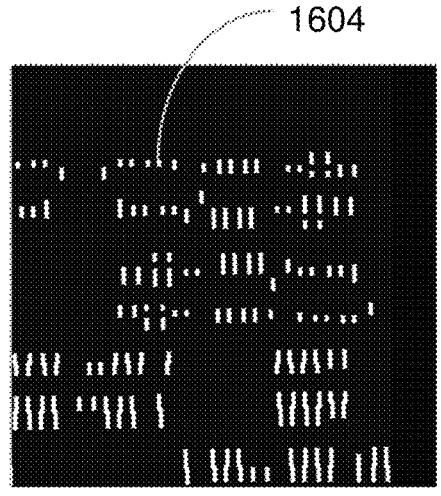
FIG. 16B shows CAD data of the active regions.
Figure 16C:
FIG. 16C shows an LVI amplitude image.
Figure 16D:
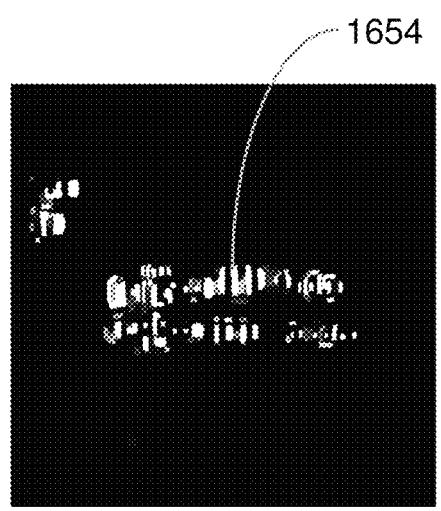
FIG. 16D shows a higher-resolution reconstructed image.

FIG. 16A shows the same CAD data 1600 (in filled-in polygon form) 1602 as in 1400 in FIG. 14A. FIG. 16B 1620 shows a generated CAD layer 1620 showing only layers consisting of active regions 1604—these layers are a subset of the patterns shown in FIG. 16A which also contains static (non-driven) layers of the DUT. FIG. 16C shows the same LVI image 1650 as in 1450 in FIG. 14. FIG. 16D shows the area 1670 from FIG. 16C after deconvolution to remove effects of the PSF, thereby sharpening the feature edges as shown. Now, registration between the features 1604 and features 1654 is successful since clearly these two sets of features appear very similar, giving greatly improved cross-correlation results between them for successful registration. Although the amplitude LVI data was used here, similar results may be obtained using phase LVI data for some embodiments. Use of amplitude data may be better in cases where the CAD data does not have values corresponding to changes in the phase LVI.

Figure 17A:
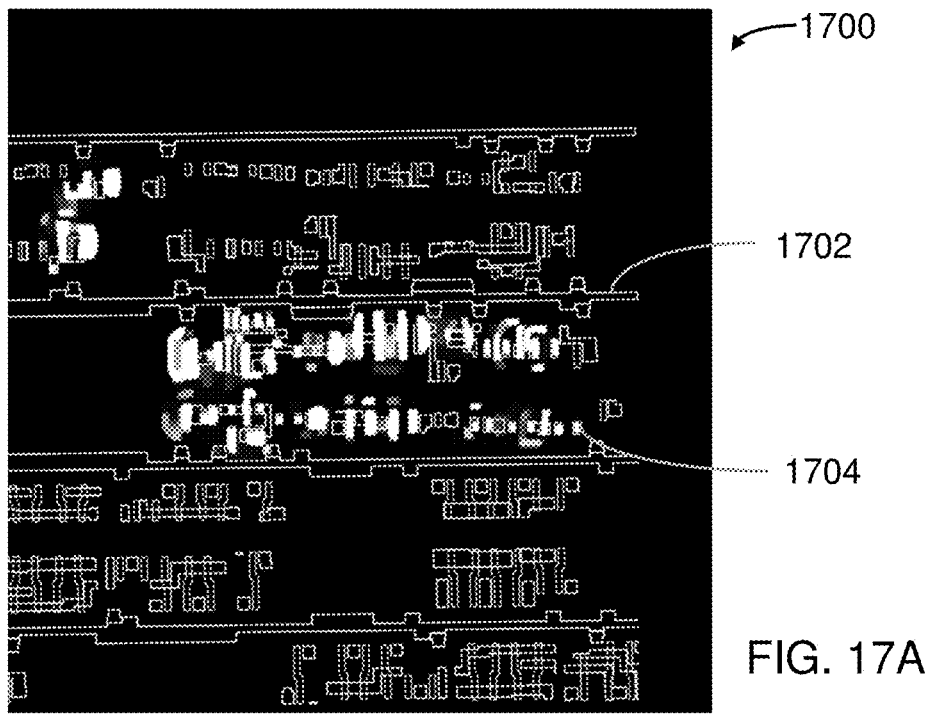
FIG. 17A shows CAD data overlaid on an LVI amplitude image in a successful alignment using embodiments of the invention.
Figure 17B:
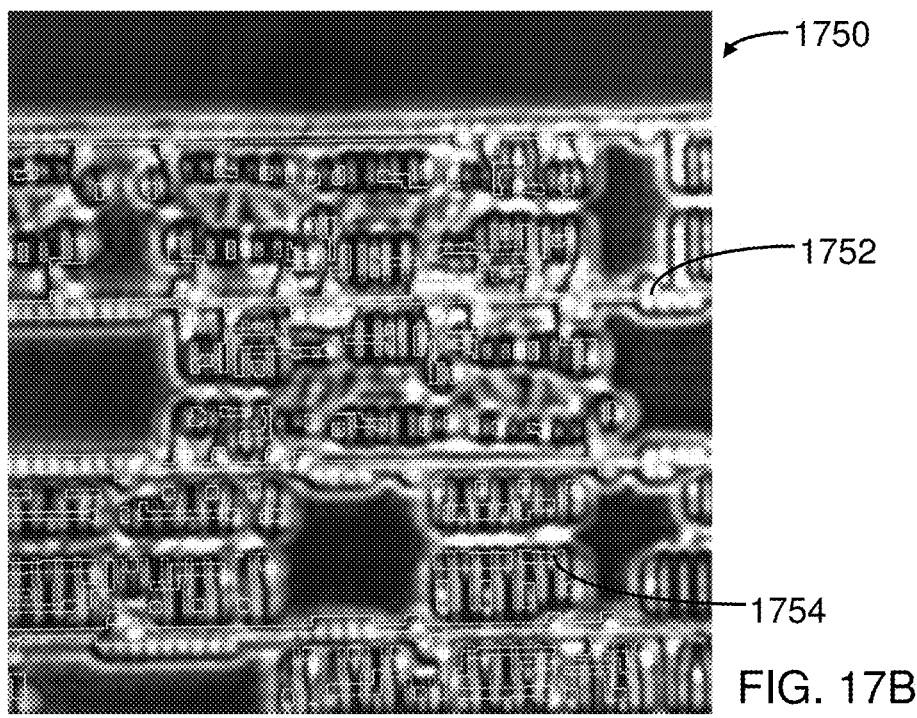
FIG. 17B shows CAD data overlaid on an LSM image in a successful alignment using embodiments of the invention.

FIG. 17A 1700 shows the CAD data 1702 from FIG. 16A and the LVI image 1704 from FIG. 16D overlaid on each other, although here the CAD data is displayed in outline form (not filled-in polygon form). Close examination shows that now the CAD data is properly registered to the underlying LVI amplitude image. FIG. 17B 1750 makes this successful registration more apparent since the LSM image 1752 has more features corresponding to patterns in the CAD data 1754, although the correlation values may not be as obvious.

Figure 18A:
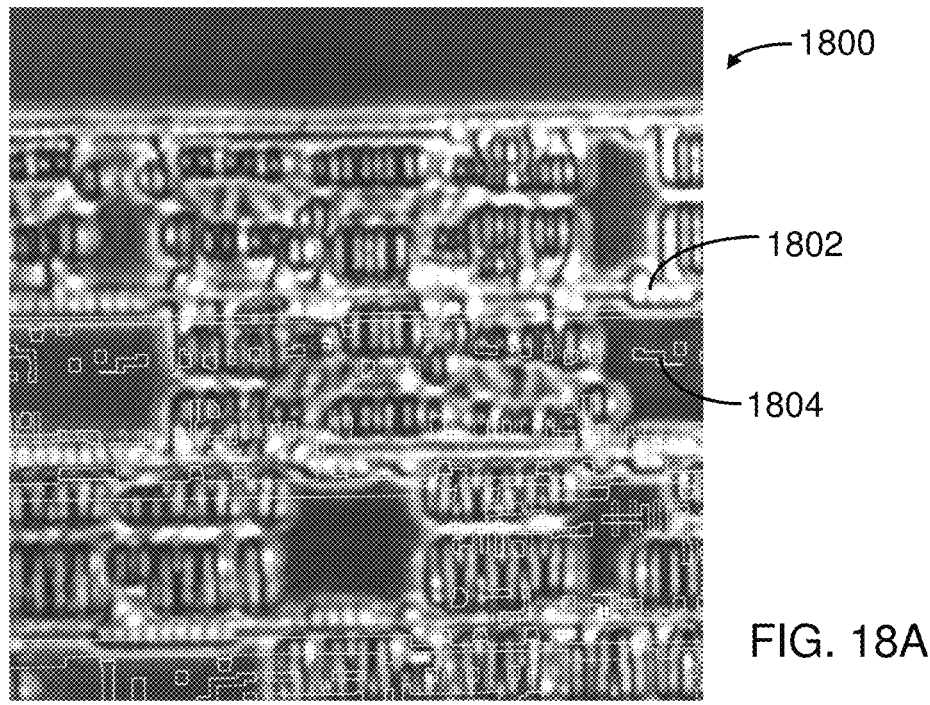
FIG. 18A shows a prior art alignment of CAD data to an image.
Figure 18B:
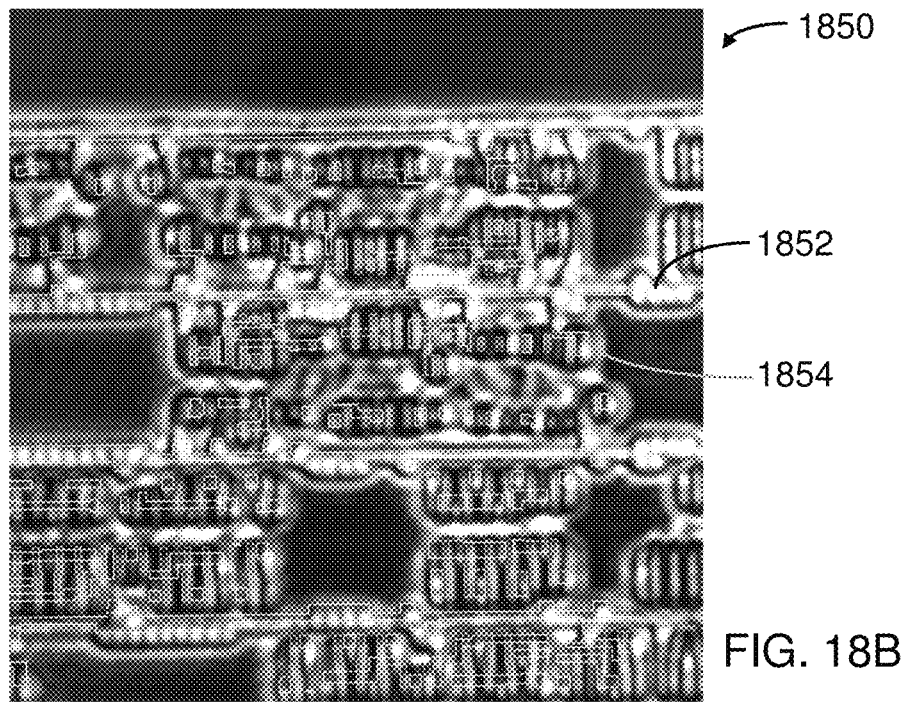
FIG. 18B shows an alignment of CAD data to an image employing the present invention.

FIG. 18A shows 1800 the misalignment of CAD data 1804 to the LSM image 1802—note the complete mismatch of features due to the failed alignment when employing these prior art methods. FIG. 18B 1850 is a successful registration between the CAD data 1852 and the LSM image 1854 accomplished using the methods of the present invention.

Although embodiments herein may refer to the use of infrared (IR) light, other embodiments employing other regions of the optical spectrum also fall within the scope of the invention.

The following are additional enumerated embodiments according to the present disclosure.

A first embodiment, which is a method for aligning computer-aided design (CAD) data optical images of at least a portion of a semiconductor device, the method comprising receiving a multiplicity of first CAD pattern layers of the semiconductor device; generating a second CAD pattern layer by an operation on the multiplicity of first CAD pattern layers; acquiring first optical images from an optical microscope; generating enhanced second images by applying image reconstruction to the first images, wherein the first images may comprise amplitude images, phase images, or both types of images; and aligning the second CAD pattern layer to the enhanced second images.

A second embodiment, which is the method of the first embodiment, wherein the optical images of at least a portion of a semiconductor device comprise Laser Voltage Imaging (LVI) images.

A third embodiment, which is the method of the first embodiment, wherein the optical images of at least a portion of a semiconductor device comprise emission images.

A fourth embodiment, which is the method of the first embodiment, wherein the operation on the multiplicity of first CAD pattern layers comprises a combination of two or more CAD pattern layers.

A fifth embodiment, which is the method of the fourth embodiment, wherein the combination of two or more CAD pattern layers comprises a Boolean logic operation.

A sixth embodiment, which is the method of the fourth embodiment, wherein the combination of two or more CAD pattern layers comprises modifications to the contrast or resolution of the two or more CAD pattern layers.

A seventh embodiment, which is the method of the first embodiment, wherein the optical microscope comprises a Solid Immersion Lens.

An eighth embodiment, which is the method of the first embodiment, wherein the image reconstruction comprises sparse reconstruction techniques.

A ninth embodiment, which is the method of the first embodiment, wherein the image reconstruction comprises quadratic or non-quadratic regularization.

A tenth embodiment, which is the method of the first embodiment, wherein the image reconstruction comprises denoising.

An eleventh embodiment, which is the method of the first embodiment, wherein the image reconstruction comprises dictionary-based regularization.

A twelfth embodiment, which is the method of the eleventh embodiment, wherein the dictionary comprises a multiplicity of patterns, and wherein the patterns comprise rectangles with varying lengths and widths, and wherein the lengths and widths are comparable to the lengths and widths of features in the semiconductor device.

A thirteenth embodiment, which is the method of the first embodiment, wherein the aligning comprises a registration operation between the second CAD pattern layer and the enhanced second images.

A fourteenth embodiment, which is the method of the thirteenth embodiment, wherein the registration operation comprises cross-correlations between the second CAD pattern layer and the enhanced second images.

A fifteenth embodiment, a system comprising a non-transitory computer-readable storage medium storing one or more programs configured to be executed by one or more computing devices, the programs when executing on the one or more computing devices, performing a method for aligning computer-aided design (CAD) data to optical images of at least a portion of a semiconductor device, the method comprising receiving a multiplicity of first CAD pattern layers of the semiconductor device; generating a second CAD pattern layer by an operation on the multiplicity of first CAD pattern layers; acquiring first optical images from an optical microscope; generating enhanced second images by applying image reconstruction to the first images, wherein the first images may comprise amplitude images, phase images, or both types of images; and aligning the second CAD pattern layer to the enhanced second images.

A sixteenth embodiment, which is the system of the fifteenth embodiment, wherein the optical images of at least a portion of a semiconductor device comprise Laser Voltage Imaging (LVI) images.

A seventeenth embodiment, which is the system of the fifteenth embodiment, wherein the optical images of at least a portion of a semiconductor device comprise emission images.

An eighteenth embodiment, which is the system of the fifteenth embodiment, wherein the operation on the multiplicity of first CAD pattern layers comprises a combination of two or more CAD pattern layers.

A nineteenth embodiment, which is the system of the eighteenth embodiment, wherein the combination of two or more CAD pattern layers comprises a Boolean logic operation.

A twentieth embodiment, which is the system of the eighteenth embodiment, wherein the combination of two or more CAD pattern layers comprises modifications to the contrast or resolution of the two or more CAD pattern layers.

A twenty-first embodiment, which is the system of the fifteenth embodiment, wherein the optical microscope comprises a Solid Immersion Lens.

A twenty-second embodiment, which is the system of the fifteenth embodiment, wherein the image reconstruction comprises sparse reconstruction techniques.

A twenty-third embodiment, which is the system of the fifteenth embodiment, wherein the image reconstruction comprises quadratic or non-quadratic regularization.

A twenty-fourth embodiment, which is the system of the fifteenth embodiment, wherein the image reconstruction comprises denoising.

A twenty-fifth embodiment, which is the system of the fifteenth embodiment, wherein the resolution-improving image reconstruction comprises dictionary-based regularization.

A twenty-sixth embodiment, which is the system of the fifteenth embodiment, wherein the dictionary comprises a multiplicity of patterns, and wherein the patterns comprise rectangles with varying lengths and widths, and wherein the lengths and widths are comparable to the lengths and widths of features in the semiconductor device.

A twenty-seventh embodiment, which is the system of the fifteenth embodiment, wherein the aligning comprises a registration operation between the second CAD pattern layer and the enhanced second images.

A twenty-eighth embodiment, which is the system of the twenty-seventh embodiment, wherein the registration operation comprises cross-correlations between the second CAD pattern layer and the enhanced second images.

In the drawings and description that follow, like parts are typically marked throughout the specification and drawings with the same reference numerals, respectively. In addition, similar reference numerals may refer to similar components in different embodiments disclosed herein. The drawing figures are not necessarily to scale. Certain features of the invention may be shown exaggerated in scale or in somewhat schematic form and some details of conventional elements may not be shown in the interest of clarity and conciseness. The present invention is susceptible to embodiments of different forms. Specific embodiments are described in detail and are shown in the drawings, with the understanding that the present disclosure is not intended to limit the invention to the embodiments illustrated and described herein. It is to be fully recognized that the different teachings of the embodiments discussed herein may be employed separately or in any suitable combination to produce desired results.

A preferred method or apparatus of the present invention has many novel aspects, and because the invention can be embodied in different methods or apparatuses for different purposes, not every aspect need be present in every embodiment. Moreover, many of the aspects of the described embodiments may be separately patentable. The invention has broad applicability and can provide many benefits as described and shown in the examples above. The embodiments will vary greatly depending upon the specific application, and not every embodiment will provide all the benefits and meet all the objectives that are achievable by the invention.

It should be recognized that some aspects of some embodiments of the present invention can be implemented via computer hardware, a combination of both hardware and software, or by computer instructions stored in a non-transitory computer-readable memory. The methods can be implemented in computer programs using standard programming techniques—including a non-transitory computer-readable storage medium configured with a computer program, where the storage medium so configured causes a computer to operate in a specific and predefined manner—according to the methods and figures described in this Specification. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits programmed for that purpose.

Further, methodologies may be implemented in any type of computing platform, including but not limited to, personal computers, mini-computers, main-frames, workstations, networked or distributed computing environments, computer platforms separate, integral to, or in communication with charged particle tools or other imaging devices, and the like. Aspects of the present invention may be implemented in machine readable code stored on a non-transitory storage medium or device, whether removable or integral to the computing platform, such as a hard disc, optical read and/or write storage mediums, RAM, ROM, and the like, so that it is readable by a programmable computer, for configuring and operating the computer when the storage media or device is read by the computer to perform the procedures described herein. Moreover, machine-readable code, or portions thereof, may be transmitted over a wired or wireless network. The invention described herein includes these and other various types of non-transitory computer-readable storage media when such media contain instructions or programs for implementing the steps described above in conjunction with a microprocessor or other data processor. The invention also includes the computer itself when programmed according to the methods and techniques described herein.

Computer programs can be applied to input data to perform the functions described herein and thereby transform the input data to generate output data. The output information is applied to one or more output devices such as a display monitor. In preferred embodiments of the present invention, the transformed data represents physical and tangible objects, including producing a particular visual depiction of the physical and tangible objects on a display.

In the following discussion and in the claims, the terms "including" and "comprising" are used in an open-ended fashion, and thus should be interpreted to mean "including, but not limited to . . . ." To the extent that any term is not specially defined in this specification, the intent is that the term is to be given its plain and ordinary meaning. The accompanying drawings are intended to aid in understanding the present invention and, unless otherwise indicated, are not drawn to scale.

Although the present invention and its advantages have been described in detail, it should be understood that various changes, substitutions and alterations can be made to the embodiments described herein without departing from the scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The various features described herein may be used in any functional combination or sub-combination, and not merely those combinations described in the embodiments herein. As such, this disclosure should be interpreted as providing written description of any such combination or sub-combination.

Many variations and modifications of the invention disclosed herein are possible, and alternative embodiments that result from combining, integrating, and/or omitting features of the embodiments disclosed herein are also within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, Rl and an upper limit, Ru, is disclosed, any number falling within the range is specifically disclosed. In particular, the following numbers within the range are specifically disclosed: R=Rl+k*(Ru−Rl), wherein k is a variable ranging from 1 percent to 100 percent with a 1 percent increment, i.e., k is 1 percent, 2 percent, 3 percent, 4 percent, 5 percent, 50 percent, 51 percent, 52 percent, 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim is intended to mean that the subject element is required, or alternatively, is not required. Both alternatives are intended to be within the scope of the claim. Use of the term "may" to introduce features of embodiments of the disclosure (e.g., "In an embodiment, the widget may be connected to a cog,") is intended to mean that embodiments reciting said features are considered to be within the scope of the invention and such embodiments shall be construed as being positively recited by the specification. However, use of the term "may" to introduce features of embodiments is not an indication that embodiments failing to recite said features are considered outside the scope of the invention. Further, although various features of embodiments are described in plural form (e.g., attachment surfaces, localized attractive sites, etc.), embodiments having single instances of said features (e.g., one attachment surface, one localized attractive site, etc.), alone or in combination with single or plural instances of other features, are also contemplated to be within the scope of the invention unless explicitly indicated otherwise. Use of broader terms such as "comprises," "includes," "having," etc. should be understood to provide support for narrower terms such as "consisting of," "consisting essentially of," "comprised substantially of," etc.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the embodiments of the present invention. The discussion of a reference in the Detailed Description of the Embodiments is not an admission that it is prior art to the present invention, especially any reference that may have a publication date after the priority date of this application.

The invention claimed is:

1. A method for aligning computer-aided design (CAD) data to optical images of at least a portion of a semiconductor device, comprising:
    receiving a multiplicity of first CAD pattern layers of the semiconductor device;
    generating a second CAD pattern layer by an operation on the multiplicity of first CAD pattern layers;
    acquiring first optical images of at least a portion of the semiconductor device from an optical microscope;
    generating enhanced second images by applying image reconstruction to the first images, wherein the first images may comprise amplitude images, phase images, or both types of images and the applied image reconstruction generates second images that are different from and improved relative to the first images;
    aligning the second CAD pattern layer to the enhanced second images.

2. The method of claim 1, wherein the optical images of at least a portion of a semiconductor device comprise Laser Voltage Imaging (LVI) images or emission images.

3. The method of claim 1, wherein the operation on the multiplicity of first CAD pattern layers comprises a combination of two or more CAD pattern layers.

4. The method of claim 3, wherein the combination of two or more CAD pattern layers comprises a Boolean logic operation.

5. The method of claim 3, wherein the combination of two or more CAD pattern layers comprises modifications to the contrast or resolution of the two or more CAD pattern layers.

6. The method of claim 1, wherein the optical microscope comprises a Solid Immersion Lens.

7. The method of claim 1, wherein the applied image reconstruction further comprises sparse reconstruction techniques.

8. The method of claim 1, wherein the image reconstruction comprises quadratic or non-quadratic regularization.

9. The method of claim 1, wherein the image reconstruction comprises denoising.

10. The method of claim 1, wherein the image reconstruction comprises dictionary-based regularization.

11. The method of claim 1, wherein the aligning comprises a registration operation between the second CAD pattern layer and the enhanced second images.

12. The method of claim 11, wherein the registration operation comprises cross-correlations between the second CAD pattern layer and the enhanced second images.

13. A non-transitory computer-readable storage medium storing one or more programs configured to be executed by one or more computing devices, the programs when executing on the one or more computing devices, performing a method for aligning computer-aided design (CAD) data to optical images of at least a portion of a semiconductor device, the method comprising:
   receiving a multiplicity of first CAD pattern layers of the semiconductor device;
   generating a second CAD pattern layer by an operation on the multiplicity of first CAD pattern layers;
   acquiring first optical images from an optical microscope;
   generating enhanced second images by applying image reconstruction to the first images, wherein the first images may comprise amplitude images, phase images, or both types of images and the applied image reconstruction generates second images that are different from and improved relative to the first images; and
   aligning the second CAD pattern layer to the enhanced second images.

14. The non-transitory computer-readable storage medium of claim 13, wherein the operation on the multiplicity of first CAD pattern layers comprises a combination of two or more CAD pattern layers.

15. The non-transitory computer-readable storage medium of claim 14, wherein the combination of two or more CAD pattern layers comprises a Boolean logic operation.

16. An optical fault analysis system, comprising:
   a backside optical imaging microscope; and
   a computer processor, programmed to align computer-aided design (CAD) data to optical images of at least a portion of a semiconductor device by performing:
      receiving a multiplicity of first CAD pattern layers of the semiconductor device;
      generating a second CAD pattern layer by an operation on the multiplicity of first CAD pattern layers;
      acquiring first optical images from the backside optical imaging microscope;
      generating enhanced second images by applying image reconstruction to the first images, wherein the first images may comprise amplitude images, phase images, or both types of images the image reconstruction generating second images that are different from and improved relative to the first images; and
      aligning the second CAD pattern layer to the enhanced second images.

17. The optical fault analysis system of claim 16, wherein the computer processor is programmed to acquire first optical images, and wherein the first optical images comprise Laser Voltage Imaging (LVI) images or emission images.

18. The optical fault analysis system of claim 16, wherein the computer processor is programmed to generate a second CAD pattern layer by an operation on the multiplicity of first CAD pattern layers, and wherein the operation comprises a combination of two or more CAD pattern layers.

19. The optical fault analysis system of claim 16, wherein the computer processor is programmed to generate enhanced second images by applying image reconstruction to the first images, and wherein the image reconstruction comprises quadratic or non-quadratic regularization.

20. The optical fault analysis system of claim 16, wherein the computer processor is programmed to generate enhanced second images by applying image reconstruction to the first images, and wherein the image reconstruction comprises dictionary-based regularization.

21. The method of claim 1 further comprising observing functional data in the optical image from a device identified by reference to the CAD data.

* * * * *